US005976553A

United States Patent [19]

Kim et al.

[11] Patent Number: 5,976,553

[45] **Date of Patent: *Nov. 2, 1999**

[54] TRANSFECTION AND GENETIC MANIPULATIONS IN OBLIGATE INTRACELLULAR PARASITES

[75] Inventors: Kami Kim, New York, N.Y.; Dominique Soldati, Wilhelmsfed, Germany; John C. Boothroyd, Stanford, Calif.

[73] Assignee: The Board of Trustees of the Leland Stanford Junior University, Stanford, Calif.

[ * ] Notice: This patent is subject to a terminal disclaimer.

[21] Appl. No.: 08/656,557

[22] Filed: May 31, 1996

Related U.S. Application Data

[63] Continuation-in-part of application No. 08/475,069, Jun. 7, 1995, abandoned, which is a continuation of application No. 08/147,783, Nov. 4, 1993, Pat. No. 5,643,718.

[51] Int. Cl.[6] .......................... A61K 39/002; C12Q 1/68; C12P 21/02

[52] U.S. Cl. .................................... 424/271.1; 424/273.1; 435/6; 435/69.1; 435/258.1; 435/258.4; 435/476; 514/44

[58] Field of Search ............................. 435/258.4, 320.1, 435/172.3, 258.1, 6, 69.1, 476; 424/271.1, 273.1; 514/44

[56] References Cited

U.S. PATENT DOCUMENTS 5,141,925 8/1992 Alroy et al. ............................. 514/23
5,187,080 2/1993 Andrews et al. ...................... 435/69.3

OTHER PUBLICATIONS

Goonewardene et al., *PNAS*, vol. 90, Jun. 1993, pp. 5234–5236.

Kim, K., Soldati, D., and Boothroyd, J.C., "Gene Replacement in *Toxoplasma gondii* with Chloramphenicol Acetyltransferase as a Selectable Marker", *Science* 262:911–914, issue of Nov. 5, 1993.

Soldati, D., Rathman, M., and Boothroyd, J.C., "Biogenesis and processing of a *Toxoplasma gondii* rhoptry protein (ROP1) with host cell penetration enhancing activity," abstract at Molecular Parasitology Meeting, Woods Hole Marine Biological Laboratories, Sep. 13–16, 1992.

Copies of 8 slides presented by D. Soldati at the Molecular Parasitology Meeting, Woods Hole Marine Biological Laboratories, Sep. 13–16, 1992.

ten Asbroek, A.L.M.A., et al., "Targeted Insertion of the Neomycin Phosphotransferase Gene into the Tubulin Gene Cluster of *Trypanosoma brucei,*" *Nature* 348:174–175 (1990).

Black, M., et al., "Restriction Enzyme–Medicated Integration Elevates Transformation Frequency and Enables Co–Transfection of *Toxoplasma gondii,*" *Mol. and Biochem. Parasitol.* 74:55–63 (1995).

Burg, J.L., et al., "Molecular Analysis of the Gene Encoding the Major Surface Antigen of *Toxoplasma gondii,*" *J. Immunol.* 141(10):3584–3591 (1988).

Burg, J.L., et al., "Direct and Sensitive Detection of a Pathogenic Protozoan, *Toxoplasma gondii*, by Polymerase Chain Reaction," *J. Clin. Microbiol.* 27(8):1787–1792 (1989).

Chamberland, S., and Current, W.L., "Use of Mouse Macrophage Cell Lines for In Vitro Propagation of *Toxoplasma gondii* RH Tachyzoites," *Proceed. Soc. Exper. Biol. Medicine* 197:150–157 (1991).

Charleston, W.A.G., "*Toxoplasma* and Other Protozoan Infections of Economic Importance in New Zealand," *New Zealand J. Zoology* 21:67–81 (1994).

Corcoran, L.M., et al., "Homologous Recombination within Subtelomeric Repeat Sequences Generates Chromosome Size Polymorphisms in *P. falciparum,*" *Cell* 53:807–813 (1988).

Cruz, A., and Beverley, S.M., "Gene Replacement in Parasitic Protozoa," *Nature* 348:171–173.

Divo, A.A., et al., "Oxygen–and Time–Dependent Effects of Antibiotics and Selected Mitochondrial Inhibitors on *Plasmodium falciparum* in Culture," *Antimicrob. Agents and Chemother.* 27(1):21–27 (1985).

Kasper, L.H., "Isolation and Characterization of a Monoclonal Anti–P30 Antibody Resistant Mutant of *Toxoplasma gondii,*" *Parasite Immunol.* 9:433–445 (1987).

Levine, N.D., and Ivens, V., *The Coccidian Parasites* (*Protozoa, Apicomplexa*) *of Carnivores*, University of Illinois Press, Urbana (1981).

Margulis, L., and Schwartz, K.V., *Five Kingdoms: An Illustrated Guide to the Phyla of Life on Earth*, W.H. Freeman and Company, New York, pp. 68–71, 86–89, and 114–117 (1982).

Nagel, S.D., and Boothroyd, J.C., "The α–and β–Tubulins of *Toxoplasma gondii* are Encoded by Single Copy Genes Containing Multiple Introns," *Mol. and Biochem. Parasitol.* 29:261–273 (1988).

Ossorio, P.N., et al., "A *Toxoplasm a gondii* Rhoptry Protein Associated with Host Cell Penetration has Unusual Charge Asymmetry," *Mol. and Biochem. Parasitol.* 50:1–16 (1992).

(List continued on next page.)

*Primary Examiner*—James Ketter
*Attorney, Agent, or Firm*—Gary R. Fabian; Charles K. Sholtz; Joanne R. Petithory

[57] ABSTRACT

A method of transient transfection of obligate intracellular parasites is described. This method is exploited to develop a system for stable transformation utilizing selectable genes. For example, introduction of the chloramphenicol acetyl transferase (CAT) gene fused to Toxoplasma flanking sequences followed by chloramphenicol selection results in parasites stably expressing CAT. DNA hybridization analysis indicated that the CAT gene had inserted via homologous recombination.

28 Claims, 9 Drawing Sheets

OTHER PUBLICATIONS

Pfefferkorn, E.R., et al., "Parasiticidal Effect of Clindamycin on *Toxoplasma gondii* Grown in Cultured Cells and Selection of a Drug–Resistant Mutant," *Antimicrob. Agents and Chemother*. 36(5):1091–1096 (1992).

Rommel, M., "Recent Advances in the Knowledge of Cyst–Forming Coccidia," *Angew. Parasitol*. 30:173–183 (1989).

Sambrook, J., et al., "Expression of Cloned Genes in Cultured Mammalian Cells," in *Molecular Cloning, A Laboratory Manual*, Second Edition, Cold Spring Harbor Laboratory Press, Cold Spring Harbor, NY (1989).

Seeber, F., and Boothroyd, J.C., "*Escherichia coli* β–Galactosidase as an In Vitro and In Vivo Reported Enzyme and Stable Transfection Marker in the Intracellular Protozoan Parasite *Toxoplasma gondii,*" *Gene* 169:39–45 (1996).

Sibley, L.D., et al., "Generation of a Restriction Fragment Length Polymorphism Linkage map for *Toxoplasma gondii,*" *Genetics* 132:1003–1015 (1992).

Soldati, D., and Boothroyd, J.C., "Transient Transfection and Expression in the Obligate Intracellular Parasite *Toxoplasma gondii,*" *Science* 260:349–352 (1995).

Soldati, D., and Boothroyd, J.C., "A Selector of Transcription Initiation in the Protozoan Parasite *Toxoplasma a gondii,*" *Mol. and Cell. Biol*. 15(1):87–93 (1995).

Soldati, D., et al., "Complementation of a *Toxoplasm gondii* ROP1 Knock–Out Mutant Using Phleomycin Selection," *Mol. and Biochem. Parasitol*. 74:87–97 (1995).

Uggla, A., "Report from a Nordic Seminar: Coccidial Infections of Ruminants—Diagnosis, Epidemiology and Control," *Bull. Scand. Soc. Parasitol*. 1:37–47 (1993).

van den Hoff, M.J.B., et al., "Electroporation in 'Intracellular' Buffer Increases Cell Survival," *Nuc. Acids. Res*. 29(11):2902 (1992).

Yoneda, A., et al., "Monoclonal Antibodies Specific for Human Chromosome 5 Obtained with a Monochromosomal Hybrid Can be Used to Sort Out Cells Containing the Chromosome with a FACS," *Chromosoma* 100:187–192 (1991).

Fig. 1
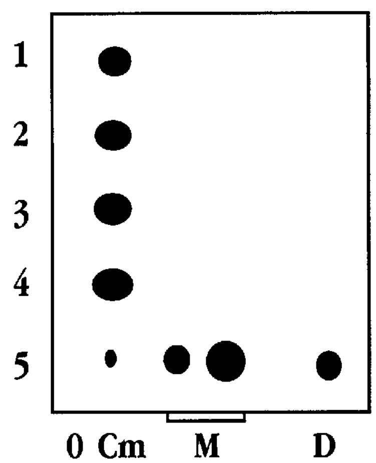
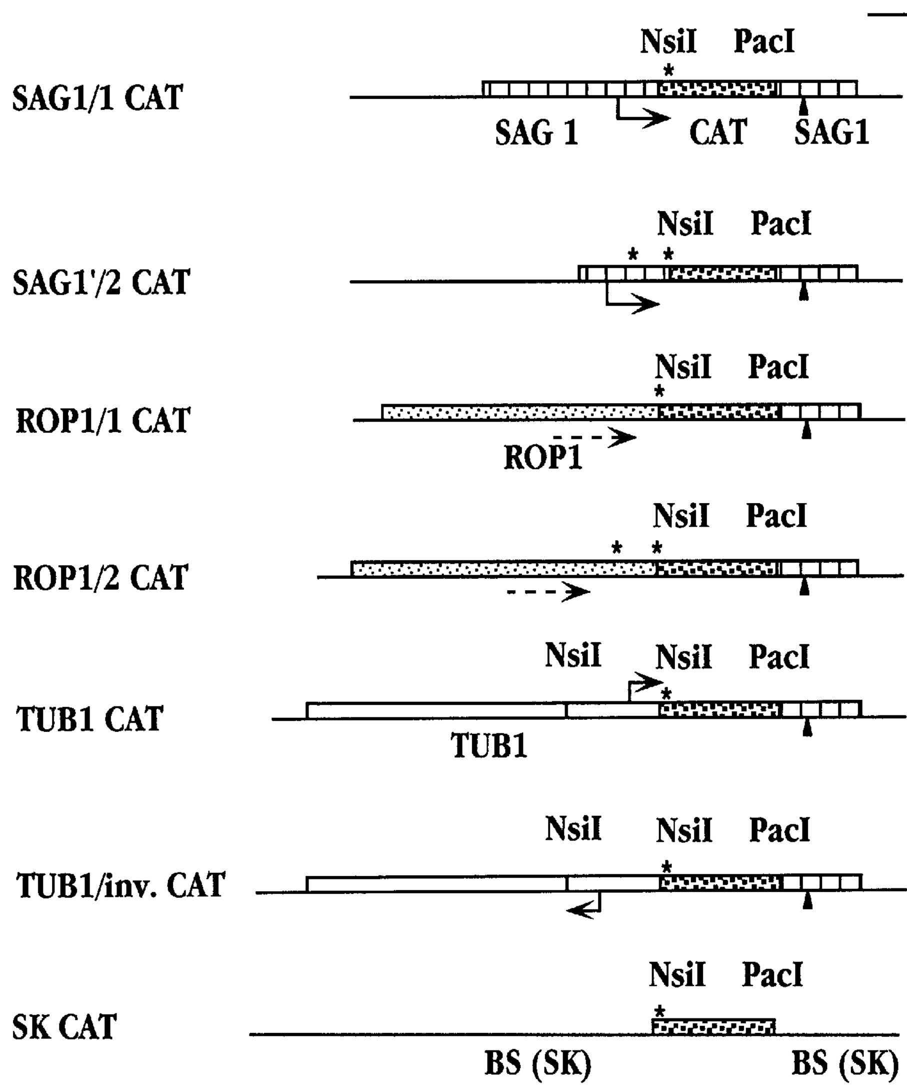
Fig. 2

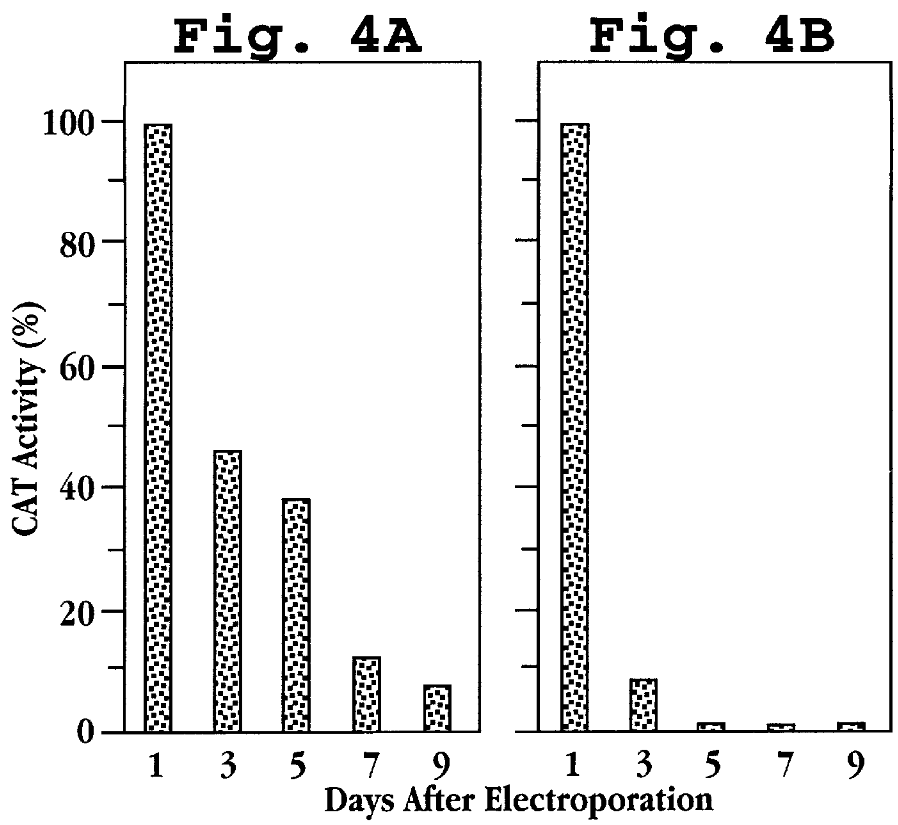
Fig. 4A
Fig. 4B
CAT Activity (%)
100
80
60
40
20
0
1 3 5 7 9
1 3 5 7 9
Days After Electroporation
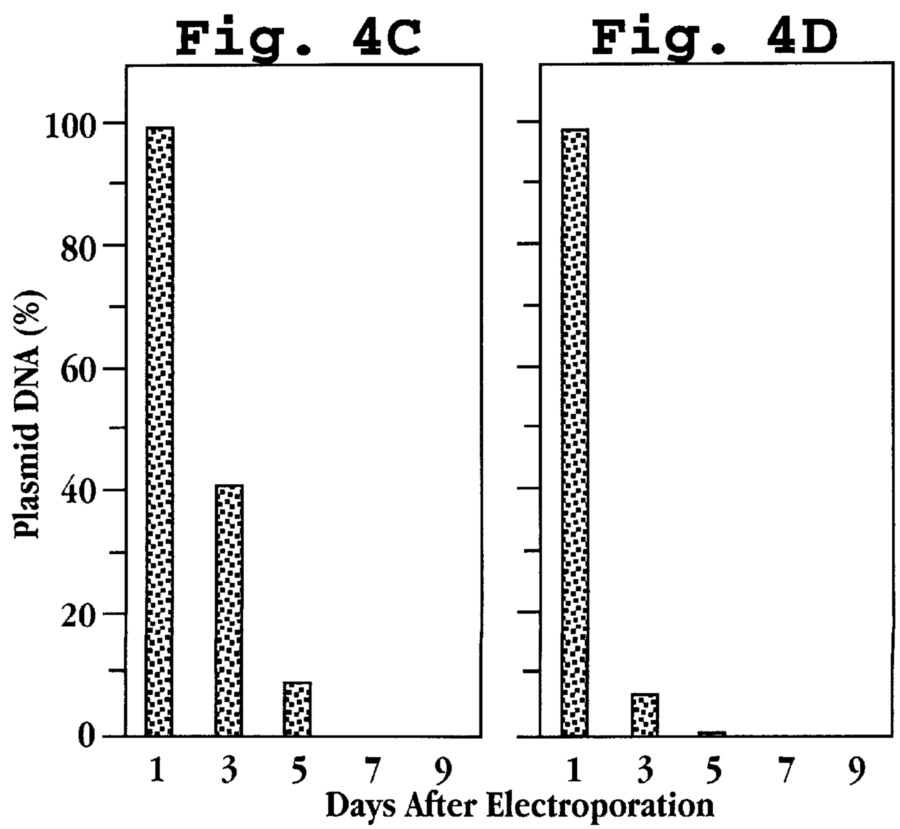
Fig. 4C
Fig. 4D
Plasmid DNA (%)
100
80
60
40
20
0
1 3 5 7 9
1 3 5 7 9
Days After Electroporation

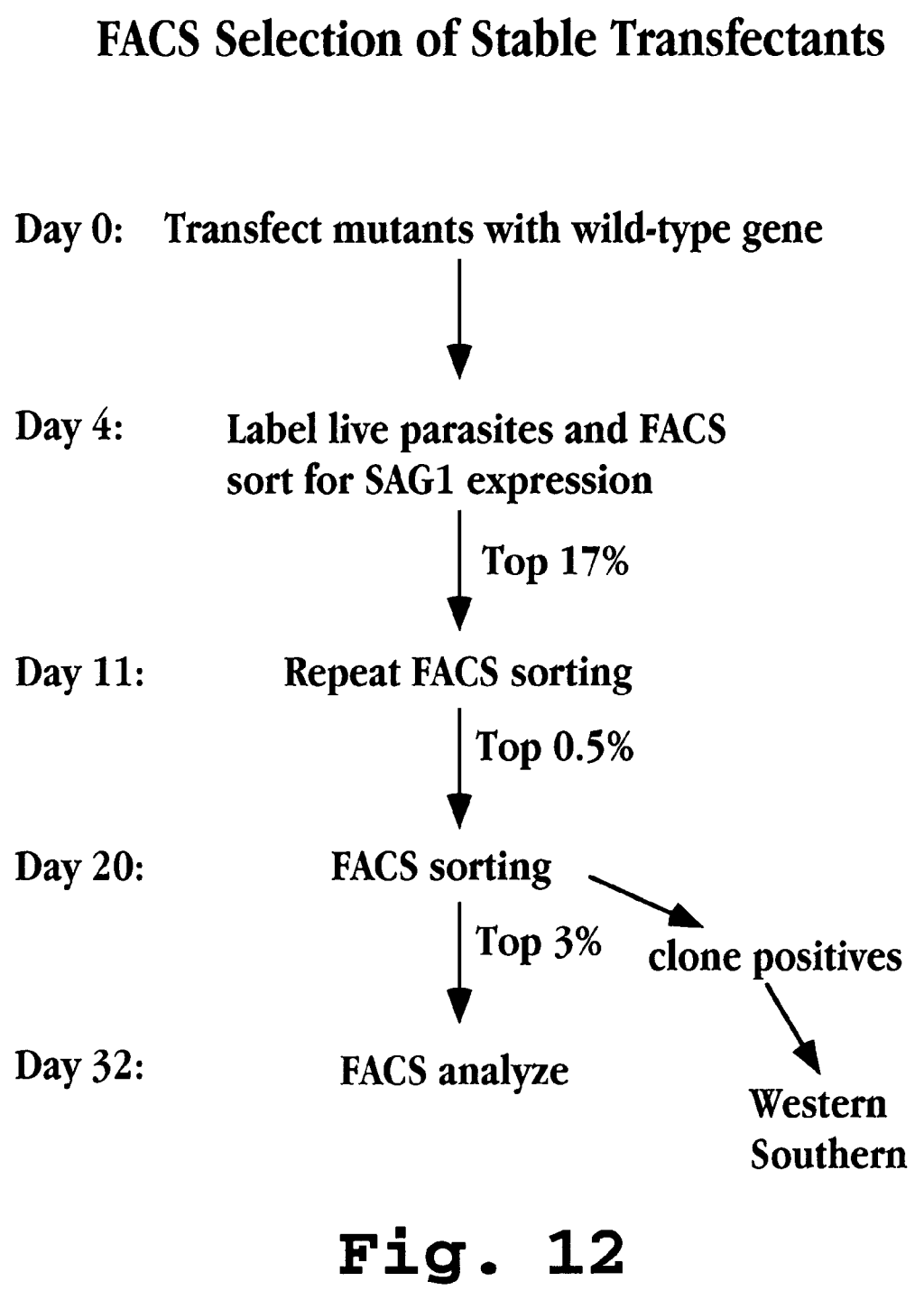

FACS Selection of Stable Transfectants

Day 0: Transfect mutants with wild-type gene

Day 4: Label live parasites and FACS sort for SAG1 expression

Top 17%

Day 11: Repeat FACS sorting

Top 0.5%

Day 20: FACS sorting

Top 3% clone positives

Day 32: FACS analyze

Western
Southern

Fig. 12

Fig. 13
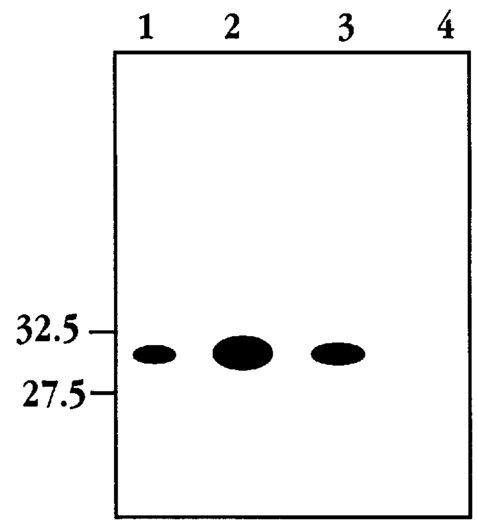
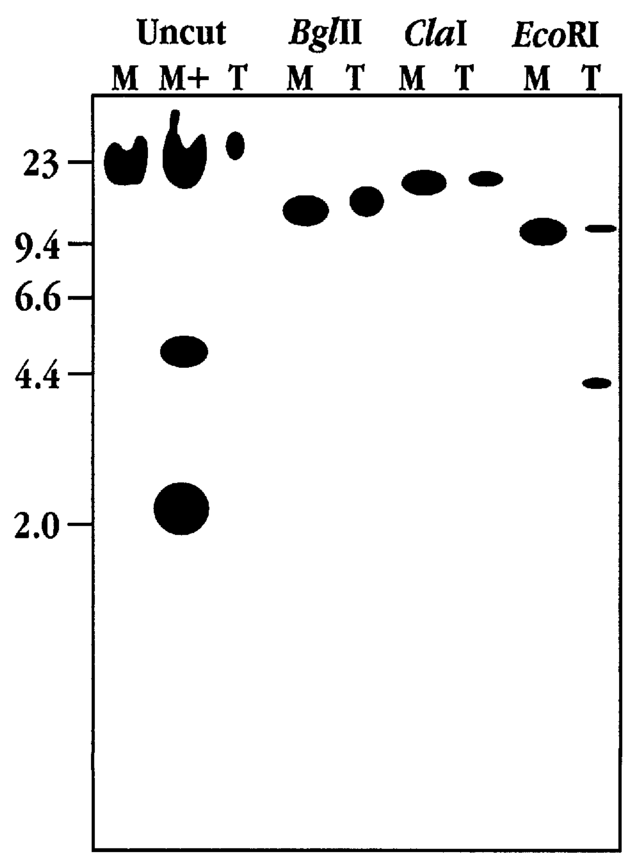
Fig. 15

TRANSFECTION AND GENETIC MANIPULATIONS IN OBLIGATE INTRACELLULAR PARASITES

This application is a continuation-in-part of U.S. patent application Ser. No. 08/475,069 filed Jun. 7, 1995, herein incorporated by reference, which is a continuation of U.S. patent application Ser. No. 08/147,783 filed Nov. 4, 1993, U.S. Pat. No. 5,643,718, herein incorporated by reference.

This invention was made with government support under National Institutes of Health grant AI21423. Accordingly, the United States government has certain rights in this invention.

FIELD OF THE INVENTION

The present invention relates to methods of transfecting and/or stably transforming obligate parasites of the phylum Apicomplexa, particularly obligate parasites of the suborder Eimeriorina.

REFERENCES

Ausubel, F. M., et al. , *CURRENT PROTOCOLS IN MOLECULAR BIOLOGY*, John Wiley and Sons, Inc., Media PA (1988).

Bellofatto, V., et al., *Science* 244:1167 (1989).

Buelow, R., and Boothroyd, J. C., *J. Imm.* 147:3496 (1991).

Burg, J. L., et al., *Immunol.* 141:3584 (1988).

Burg, J. L., *J. Clin. Microbiol.* 27:1787–1792 (1989).

Coburn, C. M., et al., *Mol. Biochem. Parasitol.* 46:169 (1991).

Coon, J. S., et al. (Eds.), *DIAGNOSTIC FLOW CYTOMETRY*, Academy of Pathology Inc. (1991).

Danneman, B., et al., *Ann. Intern Med.* 166:33–43 (1988).

de Wet, J. R., et al., *Mol. Cell. Biol.* 7:725 (1987).

Eid, J. et al., *Proc. Natl. Acad. Sci. U.S.A.* 88:2118 (1991).

Elmendorf, H. G., et al., *Mol. Biochem. Parasitol.* 52:215 (1992).

Enea, V., et al., *Proc. Natl. Acad. Sci. USA* 81:7520 (1984).

Gatignol, A., et al., *Mol. Gen. Genet.* 207(2–3): 342–348 (1987).

Gorman, C. M., et al., *Mol. Cell. Biol.* 2:1044 (1982).

Harlow, E., et al., *ANTIBODIES: A LABORATORY MANUAL*, Cold Spring Harbor Laboratory Press, Cold Spring Harbor, N.Y. (1988).

Hitzeman, R. A., et al., U.S. Pat. No. 4,775,622, issued Oct. 4, 1988.

Jefferies, D. et al., *Nucleic Acids Res.* 21(2): 191–195 (1993).

Kasper, L. H., et al., *J. Immunol.* 132:443–449 (1984).

Kasper, L. H., et al., *J. Clin. Invest.* 75:1570 (1985).

Kasper, L. H., et al., *Parasite Immunol.* 9:433 (1987).

Kasper, L. H., et al., in *IMMUNOLOGY OF PARASITIC DISEASES*, (Warren, K. et al., Eds. ), Blackwell Scientific, Oxford, United Kingdom, pp. 264–299 (1992a).

Kasper, L. H., et al., *J. Imm.* 148:9805 (1992b).

Keren, D. F., (Ed.), in *FLOW CYTOMETRY IN CLINICAL DIAGNOSIS*, American Society of Clinical Pathologists (1989).

Laban, A., et al., *Proc. Natl. Acad. Sci. USA* 86:9119 (1989).

Laban, A., et al., *Nature* 343:572–574 (1990).

LeBowitz, C. M., et al., *Proc. Natl. Acad. Sci. USA* 87:9736 (1990).

Lee, M. G. -S., et al., *Science* 250:1583 (1990).

Maniatis, T., et al., in *MOLECULAR CLONING: A LABORATORY MANUAL*, Cold Spring Harbor Laboratory, Cold Spring Harbor, N.Y. (1982).

Margulis, L., and Schwartz, K. V., in *FIVE KINGDOMS, AN ILLUSTRATED GUIDE TO THE PHYLA OF LIFE ON EARTH*, W. H. Freeman & Co. (1982).

Medina-Acosta, E. and Cross, G., *Molec. Biochem. Parasitol.* 59:327–30 (1993)

Miller, et al., in *RECENT ADVANCES IN AVIAN IMMUNOLOGY RESEARCH*, Alan R. Liss, Inc., pp. 117–130 (1989).

Mineo, J. R., et al., *J. Immunol.* 150:3951–3964 (1993).

Nagel, S. D., et al., *Mol. Biochem. Parasitol.* 29:261 (1988).

Neuman, J. R., et al., *BioTechniques* 5:444–447 (1987).

Obrig, T. G., et al., *J. Biol. Chem.* 246:174 (1971).

Oeda, K., et al., U.S. Pat. No. 4,766,068, issued Aug. 23, 1988.

Ossorio, P. N., *Mol. Biochem. Parasitol.* 50:1 (1992).

Pearson, W. R. and Lipman, D. J., *PNAS* 85:2444–2448 (1988).

Pearson, W. R., *Methods in Enzymology* 183:63–98 (1990).

Perez, P., et al., *Plant Mol. Biol.* 13(4):365–373 (1989).

Pfefferkorn, E. R., et al., *Exp. Parasitol.* 39:365 (1976).

Pfefferkorn, E. R., et al., *Antimicrob. Agents Chemother* 36:1091–1096 (1992).

Prince, J. B., et al., *Mol. and Biochem. Parasitol.* 43(1):97 (1990).

Rutter, W. J., et al., U.S. Pat. No. 4,769,238, issued Sep. 6, 1988.

Sambrook, J., et al., in *MOLECULAR CLONING: A LABORATORY MANUAL, SECOND EDITION*, Cold Spring Harbor Laboratory Press, Cold Spring Harbor, N.Y. (1989).

Seeber, F and J. C. Boothroyd, *Gene* 169:39–45 (1996).

Sibley, L. D., et al., *Genetics* 132:1003 (1992a).

Sibley, L. D., *Mol. Biochem. Parasit.* 51:291–300 (1992b).

Tanabe, K., et al., *Jpn. J. Parasitol.* 26:113 (1977).

Tobin, J. F., et al., *Proc. Natl. Acad. Sci. USA* 88:864 (1991).

Triglia, T., et al., *Nucleic Acids Res.* 16:8186 (1988).

Van den Hoff, M. J. B., et al., *Nucleic Acids Res.* 20:2902 (1992).

BACKGROUND OF THE INVENTION

*Toxoplasma gondii* is an obligate intracellular parasite which can infect most warm-blooded vertebrates. In humans, it has been recognized as a major cause of severe congenital disease and a common cause of infection in immunocompromised hosts. Recently, the parasite has received increased attention as an important opportunistic pathogen affecting up to 25% of AIDS patients (Kasper, 1992a). In the laboratory, *T. gondii* is relatively easy to handle and maintain and consequently has become an important model for the study of how obligate intracellular parasites function. To date, however, such studies have been hampered by the absence of a method for introducing DNA into the parasites.

Although transfection and stable transformation have been achieved for a range of trypanosomatids (Bellofatto, et al., 1989; Laban, et al., 1989, 1990; Lee, et al., 1990; Coburn, et al., 1991; Eid, et al., 1991; Lebowitz, et al., 1990; and Tobin, et al., 1991), such methodologies have not been reported for any of the obligate intracellular parasites, most notably members of the phylum Apicomplexa.

Efforts to stably transform these parasites have been complicated by their inability to replicate outside host cells. Neomycin and hygromycin, drugs commonly used for selection of stable transformants in other systems, including protozoan parasites from the kinetoplastida order (Laban, et al., 1989; Lee, et al., 1990; Coburn, et al., 1991), kill host cells as efficiently as parasites.

SUMMARY OF THE INVENTION

The present invention teaches a method for transfecting an obligate intracellular parasite of the phylum Apicomplexa, preferably of the class Sporozoasida, more preferably of the subclass Coccidiasina. The subclass Coccidiasina includes the order Hemosporidia, which contains the genus Plasmodium, the causative agent of human malaria. Coccidiasina also includes the order Eucoccidiorida which includes the suborder Eimeriorina. In one embodiment, the parasite belongs to the order Hemosporidia (e.g., Plasmodium). In a preferred general embodiment, the parasite belongs to the order Eucoccidiorida. In a particularly preferred embodiment, the parasite belongs to the suborder Eimeriorina, which includes such genera as Toxoplasma, Eimeria, Sarcocystis, Neospora, Cryptosporidium, Hammondia and Besnoitia.

In the method of the present invention, a vector is provided that contains a DNA sequence. Typically, this DNA sequence encodes a protein and is flanked by regulatory elements effective to allow expression of the sequence in the parasite cells. Such regulatory elements include, but are not limited to, transcription/translation initiation and/or termination sequences. The DNA sequence may encode a protein homologous to the parasite being transformed: for example, if the parasite is Toxoplasma, the DNA sequence may correspond to the SAG1 gene. Alternatively, the DNA sequence may encode a genetically selectable marker gene (such as, a gene that encodes a protein which confers resistance to a selected antibiotic). Such selectable marker (or reporter) genes include the chloramphenicol acetyltransferase (CAT) gene and the ble gene from Tn5.

In addition, the vector can contain a DNA sequence which is homologous to a portion of the genomic DNA of the parasite (e.g., the B1 region of Toxoplasma). Such sequences allow integrative transformation. The vector may also contain further DNA sequences which allow replication (e.g., an origin of replication) and selection (e.g., a gene encoding ampicillin resistance) in alternative hosts, thus allowing the propagation and purification of such vectors outside of the parasite. Alternative hosts include, but are not limited to, bacteria and yeast.

The vector can be linear or circular and is introduced into the parasite cell, typically by electroporation in a selected buffer (e.g., cytomix, described herein).

Transfected parasites are then identified by selecting for the presence of the vector in the parasite. Typically, this is done by examining the parasites for the production of a protein, encoded by the vector, that the host parasite is incapable of producing (or in which the parasite is impaired in production of the protein). In one embodiment, a DNA sequence contained in the vector encodes a protein that confers drug resistance to a selected drug. The target parasite must be susceptible to the effects of the drug in the absence of the protein. For example, if the CAT gene were used, chloramphenicol can be added to the media at a concentration effective to kill non-transformed parasites but not transformed parasites. Phleomycin (and other members of the bleomycin family) can be used in similar fashion when the ble gene is used.

In another embodiment of the present invention, the vector carries DNA sequences encoding a surface antigen protein not present on the surface of the non-transformed host parasite. Such surface antigens may be fusion proteins between known parasite surface antigens and heterologous or exogenous proteins (e.g., SAG1 coding and leader sequences fused in frame to coding sequences for a T-cell surface antigen). In this method, the transformed cells are selected by identifying the cells expressing the vector-encoded-surface-antigen. One method of transformed cell selection is flow cytometry, specifically, fluorescence activated cell sorting. In this method, a fluorescence-labeled antibody is either directly or indirectly bound to the surface antigen.

In the indirect method, one antibody immunoreactive with the surface antigen is bound to the antigen and then a second labeled antibody, immunoreactive with the first antibody, is added. In the direct method, the antibody that is immunoreactive with the surface antigen is directly labeled with the fluorescent probe. Antibodies used in the practice of the present invention can be monoclonal or polyclonal as long as they are specifically and selectively immunoreactive with the selected surface antigen. One alternative method to FACS is traditional immunological panning for cell separation.

The transfection method of the present invention can be used to generate cell surface antigen deletion mutants in the target parasite. The coding region of a clone encoding a wild type copy of the gene is deleted and the resulting construct is transfected into parasites. The transfected parasites are screened with antibodies for parasites that no longer express the antigen of interest, indicating replacement of the wild-type gene with the deleted version.

The present invention also includes obligate intracellular parasites of the phylum Apicomplexa transformed by the method of the present invention, where the parasite carries a DNA sequence exogenous to said intracellular parasite. Such transformants may carry the exogenous DNA sequence extra-chromosomally or integrated in their genomes.

The transformed obligate parasites are preferably of the class Sporozoasida, more preferably of the subclass Coccidiasina. In one embodiment, the parasites belong to the order Hemosporidia (e.g., Plasmodium). In a preferred general embodiment, the parasites belong to the order Eucoccidiorida. In a particularly preferred embodiment, the parasites belong to the suborder Eimeriorina, which includes such genera as Toxoplasma, Eimeria, Sarcocystis, Neospora, Cryptosporidium, Hammondia and Besnoitia.

The invention further includes expression vectors useful for transformation of an obligate intracellular parasite of the phylum Apicomplexa (preferable embodiments as listed above). A number of exemplary plasmid constructs are described with reference to the parasite Toxoplasma.

In yet another embodiment, the invention provides a method for the recombinant expression of a protein in a host infected with an obligate intracellular parasite of the phylum Apicomplexa (preferable taxonomically-defined embodiments as listed above). In this method, a vector is constructed containing a DNA sequence encoding the gene of interest. The DNA sequence is flanked by regulatory elements effective to allow expression of the encoded protein in a parasite host cell. The vector is introduced into the parasites and infected into host cells. The host cells are then cultured under conditions permissive for the expression the protein.

These and other objects and features of the invention will be more fully appreciated when the following detailed description of the invention is read in conjunction with the accompanying drawings.

BRIEF DESCRIPTION OF THE FIGURES

FIG. 1 shows the results of thin-layer chromatography of acetylated forms of radioactively labeled chloramphenicol after incubation in lysates of cells transfected with the chloramphenicol acetyltransferase (CAT) expression construct SAG1/2 CAT.

FIG. 2 presents a schematic description of six expression plasmids.

FIGS. 4A, 4B, 4C and 4D show the results of the analysis of transience of transfection using two populations of recombinant parasites electroporated with either TUB1 CAT (4A and 4C) or ROP1/2 CAT (4B and 4D) plasmids. FIGS. 4A and 4B present CAT expression data. FIGS. 4C and 4D present CAT DNA hybridization data.

FIG. 12 presents a schematic of the identification of rescued sag1- transformants using FACS selection and sorting.

FIG. 13 presents the results of protein blot examination of proteins produced by stable transformants.

FIG. 15 shows the results of a genomic DNA hybridization analysis which indicated that a single copy of SAG1 had integrated into the genome of each transfectant.

DETAILED DESCRIPTION OF THE INVENTION

I. Definitions

Figure 3:
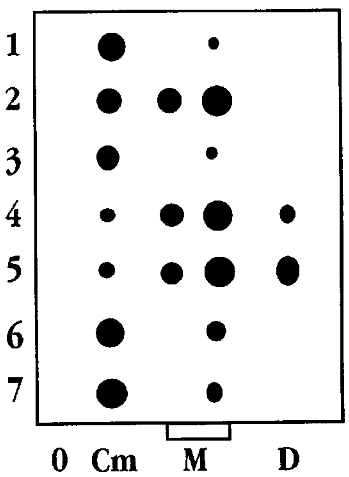
FIG. 3 chloramphenicol acetyltransferase (CAT) gene expression in $10^7$ extracellular *T. gondii* parasites transfected using six different *T. gondii* expression vectors.

Endogenous DNA refers to DNA not introduced into the parasite by recombinant means.

Exogenous DNA refers to DNA which has been transfected into parasite cells. Exogenous DNA refers to DNA that is not originally derived from the transfected or transformed cells' genomic DNA (e.g., CAT and ble gene sequences).

Extra-chromosomal DNA refers to plasmid DNA introduced into a parasite cell, where the plasmid DNA has not integrated into the genomic DNA of the parasite.

"Sequence similarity" or "sequence homology", e.g., between two DNA sequences, is determined essentially as follows. Two polynucleotide sequences of comparable length are considered to be similar to one another, if, when they are aligned using the ALIGN program, over 60%, preferably 65% or 75%, or more preferably 85% of the nucleic acids in the highest scoring alignment are identically aligned using a ktup of 1, the default parameters and the default PAM matrix. Note that a "similarity" analysis such as described above may be applied to a portion of a sequence, for example, to identify a common motif or motifs among proteins having regions of similarity as well as regions of divergence.

The ALIGN program is found in the FASTA version 1.7 suite of sequence comparison programs (Pearson, et al., 1988; Pearson, 1990; program available from William R. Pearson, Department of Biological Chemistry, Box 440, Jordan Hall, Charlottesville, Va.).

In the absence of specific sequence information, two nucleic acid fragments are considered to be "selectively hybridizable" to one another if they are capable of specifically hybridizing to one another: (i) under typical hybridization and wash conditions, as described, for example, in Maniatis, et al. (1988), pages 320–328, and 382–389, or (ii) using reduced stringency wash conditions that allow at most about 25–30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each.

Preferably, highly similar nucleic acid strands contain less than 20–306 basepair mismatches, even more preferably less than 5–209 basepair mismatches. These degrees of similarity or homology can be selected by using wash conditions of appropriate stringency for identification of clones from gene libraries (or other sources of genetic material), as is well known in the art.

A polynucleotide or polypeptide is "derived from" a particular organism if that polynucleotide or polypeptide was originally isolated from that organism. For example, a polynucleotide in a plasmid propagated in *E. coli* is derived from Toxoplasma if that polynucleotide was originally isolated from Toxoplasma mRNA, genomic DNA or cDNA. Alternatively, a polynucleotide or polypeptide is "derived from" a particular organism if the sequence of that polynucleotide or polypeptide is based on the sequence of the corresponding sequence from that organism. For example, a polypeptide is derived from Toxoplasma if the sequence of the polypeptide is the same as the sequence of the corresponding native Toxoplasma polypeptide.

II. Apicomplexa Taxonomy

The Apicomplexa are spore-forming parasites of animals. They reproduce sexually, with alternation of haploid and diploid generations (Margulis and Schwartz, 1982). The phylum is named for the "apical complex", an arrangement of fibrils, microtubules, vacuoles and other organelles at one end of each cell.

The Apicomplexa include hundreds of species, which are further divided into two classes (Sporozoasida and Piroplasmasida) and a number of subclasses, orders and suborders. Sporozoasida in turn includes subclasses Coccidiasina and Gregarinasina. The subclass Coccidiasina includes the order Hemosporidia, which contains the genus Plasmodium, the causative agent of human malaria. Coccidiasina also includes the order Eucoccidiorida, also termed coccidia, which includes the suborder Eimeriorina. The suborder Eimeriorina includes, but is not limited to, the following genera: Toxoplasma, Eimeria, Sarcocystis, Neospora, Isospora, Cryptosporidium, Hammondia and Besnoitia.

Coccidians are among the best known of the apicomplexans due to their propensity to cause serious, sometimes fatal, disease in their animal hosts. Toxoplasma, Sarcocystis and Besnoitia typically cause diseases in the parenteral organs of the affected host, while Eimeria and Isospora generally cause diseases in the digestive tract (e.g., coccidiosis). The majority of Eimeria and Isospora attack the intestinal epithelium, with severe cases causing bloody diarrhea, dehydration, emaciation and death.

The parasites have a broad host range. For example, Eimeria species alone infect chickens, cattle, sheep, goats and pigs. Further, they are responsible for large world-wide economic losses, with the loss to the poultry industry alone estimated at $1,800 million annually (Miller, et al., 1989).

Although most coccidians affect livestock and/or fowl, others can also infect humans. For example, Toxoplasma gondii can cause severe congenital disease and be a common cause of infection in immunocompromised human hosts—it affects up to 25% of AIDS patients as an opportunistic pathogen (Kasper, 1992a). Isospora hominis directly parasitizes man.

The methods and compositions herein are exemplified in most cases using *Toxoplasma gondii*. It will be understood, however, that these methods may be similarly applied to any parasite of the Phylum Apicomplexa. The methods are particularly effective, however, with respect to parasites in the subclass Coccidiasina, and further, in the order coccidians, suborder Eimeriorina. Examples of genera in this suborder include Toxoplasma, Eimeria, Sarcocystis, Neospora, Isospora, Cryptosporidium, Hammondia and Besnoitia.

III. Transfection of Obligate Intracellular Parasites

Experiments performed in support of the present invention demonstrate that electroporation of *Toxoplasma gondii* (*T. gondii*) in potassium phosphate-based electroporation buffer (cytomix) a buffer that resembles the cytosol's ionic composition (Van den Hoff, et al., 1992), gives an extremely good rate of cell survival. Typically, approximately 80% of the parasites are capable of invading host cells after electroporation (as compared with the same population of parasites not subjected to an electric pulse).

For use as a reporter construct, a plasmid (SAG1/2 CAT) was made containing the chloramphenicol acetyltransferase (CAT) gene (Gorman, et al., 1982) and the upstream and downstream sequences of the *T. gondii* major surface antigen gene, p30 or SAG1 (Burg, et al., 1988) (Example 1). *T. gondii* genes other than SAG1, as well as genes obtained from other obligate intracellular parasites, can be employed in similar fashion. Further, other reporter genes may be used as well, for example, the firefly luciferase gene (de Wet, et al., 1987).

Electroporation of this construct into freshly purified, extracellular *T. gondii* (Example 2), followed by incubation for 16 hours in medium, resulted in substantial levels of CAT activity (Example 3, FIG. 1). Neither the host cells [human foreskin fibroblasts (HFF)] nor *T. gondii* had any detectable intrinsic CAT activity, and there was no significant level of expression of SAG1/2 CAT in electroporated HFF cells alone.

Invading parasites could not passively have delivered the plasmid to host cells because no CAT activity was seen when plasmid, parasites, and host cells were incubated together in the absence of electroporation.

The possibility that expression is due to transfection of a contaminant (such as bacteria) in the medium or buffer can be excluded on several grounds. First, electroporation of host cell cultures treated as though infected gave no activity (FIG. 1). Second, all reagents, including electroporated parasites, were plated on rich (L broth) agar, and no growth of any contaminating organisms was seen after incubation for 2 days. Third, no CAT activity was detectable when transfected parasites were incubated in medium containing 100 $\mu$g of cycloheximide per milliliter, indicating that expression was exclusively dependent on eukaryotic translational machinery (Obrig, et al., 1971; Elmendorf, et al., 1992).

Because the parasites subjected to the electric pulse were still capable of invading host cells, the CAT activity generated by electroporated parasites incubated in Dulbecco's minimum essential medium (DMEM) containing 20% Nu serum (Gibco/BRL, Gaithersberg, Md.) for 16 hours was compared to that of parasites introduced onto a fibroblast monolayer 2 hours after transfection and then incubated for 14 hours. Both conditions gave the same CAT activity, which implies that extracellular parasites are biosynthetically active for an extended period.

No CAT was detectable immediately after electroporation; the earliest detectable activity was at about 4 hours after the electroporation and rose steadily through the first 24 hours. Hence, CAT enzyme was not contaminating the plasmid DNA preparation which was, in any case, phenol-extracted and purified by cesium chloride banding.

The results described above demonstrate that measuring CAT enzymatic activity reflects both DNA uptake and expression by *T. gondii*. The enzymatic activity was proportional to the number of parasites present, over a range of $10^6$ and $5.10^7$ parasites. It was also proportional to the amount of plasmid in the 5- through 150- $\mu$g range. In practice, a readily detectable signal can be obtained 16 hours after electroporation, with $10^6$ parasites and as little as 5 $\mu$g of plasmid. Optimal electroporation parameters were found to be 2.0 kV and 48 ohm, with an extremely low time constant of 0.40 to 0.45 ms owing to the salt composition of the cytomix buffer. The electroporation conditions can be altered to achieve varying levels of transfection efficiency.

The efficiency of the transfection, in terms of the proportion of the parasites expressing the transfected gene, could not be assessed with the CAT construct. It is not possible to measure the CAT activity of individual parasites. Further, commercial antibodies to CAT cross-react with a range of Toxoplasma antigens. An indication of the transfection efficiency, however, can be made from experiments in which 100 μg of a construct bearing the intact SAG1 gene was transfected, using the method of the present invention, into a SAG1- mutant. Using a cell sorter and a monoclonal antibody specific for the SAG1 gene product, approximately 15% of the electroporated parasites were found to express the transfected gene 4 days after electroporation.

IV. Other Vectors Useful in Transfection of Intracellular Parasites

For generating vectors for the expression of exogenous DNA (DNA not originally derived from the parasite being transformed), transcriptional and translational regulatory sequences (including initiation and termination sequences) are typically obtained from 5' and 3' non-coding regions of genes; as described above for SAG1. The ability of the following 5' regions, from two other *T. gondii* genes, to mediate expression of CAT was also evaluated: TUB1 (Nagel, et al., 1988), encoding α-tubulin; and ROP1 (Ossorio, 1992), encoding a protein found in the specialized secretory organelles of the apical complex called rhoptries.

FIG. 2 shows a schematic description of six expression plasmids (not to scale). The black box indicates the CAT coding region upstream of an ATG start codon (marked with an asterisk) or downstream of the TAG stop codon and including the transcription start site (bent arrow) and polyadenylate-addition site (triangle). Grey boxing indicates sequences from ROP1 (Ossorio, 1992), and the open box represents sequences from TUB1 region (Nagel, et al., 1988), beginning with an ATG start codon and proceeding upstream for ~1.35 kb and ~3 kb, respectively. The precise transcription start point for ROP1 is not known. The number after the slash indicates whether the first or second in-frame ATG of the SAG1 or ROP1 gene is at the start of the CAT cassette.

SAG1/1 CAT was generated essentially as described for SAG1/2 CAT except that the upstream reverse polymerase chain reaction (PCR) primer extended from the first in-frame ATG of the SAG1 gene: hence, this is the ATG driving CAT.

SAG1'/2 CAT is identical to SAG1/2 CAT except that it is missing a region of about 400 bp of the region upstream of SAG1. The deleted region was found to have no effect on CAT expression.

Plasmids ROP1/1 CAT and ROP1/2 CAT were generated by replacement of the 5' flanking region of the SAG1 gene in the SAG1'/2 CAT construct with PCR-generated fragments of the upstream sequences of ROP1. These fragments terminated at either the first or the second ATG of ROP1 for the ROP1/1 and ROP1/2 constructs, respectively.

In plasmid TUB1 CAT, the upstream sequence of SAG1'/2 CAT has been replaced by about 3 kb of 5' flanking region of the TUB1 gene. In all cases the sequences immediately upstream of the start codon and downstream of the stop codon are derived from the indicated *T. gondii* gene. In plasmid TUB1/inv. CAT, a segment of about 500 bp immediately upstream of the ATG, including the transcription start site, is inverted.

Each of these constructs was transfected into *T. gondii*, and the resulting CAT activities were assayed (Example 4, FIG. 3). Although the expression vectors derived from all three genes were highly active, quantitation of these results from assays in the linear range reproducibly showed that the TUB1 CAT and ROP1/2 CAT constructs yield about eightfold and fourfold more CAT than SAG1'/2 CAT, respectively.

The CAT cassette present in a plasmid vector that had no *T. gondii* sequences (SK CAT) showed virtually no activity. Addition of the 3' sequences of SAG1 downstream of the CAT cassette in SK CAT gives the same minimal activity.

On the basis of the DNA sequence analysis (Nagel, et al., 1988; Ossorio, 1992), there are two plausible ATG start codons for SAG1 and ROP1 translation. Placement of the CAT cassette adjacent to the first ATG of either gene (SAG1/1 CAT and ROP1/1 CAT) gave rise to no significant activity (as compared with the SK CAT control) (FIG. 3, lanes 1 and 3, respectively). However, placement immediately downstream of the second ATG (SAG1/2 CAT and ROP1/2 CAT) gave rise to high activity for both (FIG. 3, lanes 2 and 4, respectively). These data are consistent with predictions (Nagel, et al., 1988; Ossorio, 1992) of which ATG functions in vivo based on ATG context and distance from the predicted (ROP1) or known (SAG1) signal peptide cleavage site (both proteins pass through the secretory pathway).

The use of CAT gene-specific antisense oligonucleotide primers showed comparable amounts of transcript of the expected size in parasites receiving SAG1/1 CAT and SAG1'/2 CAT. Accordingly, the differential expression of these constructs appears to be posttranscriptional based on the primer extension analysis of RNAs isolated from parasites transfected with the two constructs.

The transience of the transfection was evaluated for a 9-day period after electroporation by measurement of the longevity of CAT expression (Example 5, FIGS. 4A and 4B) and by slot-blot quantitation of the presence of the transfecting plasmid (Example 5, FIGS. 4C and 4D). During this period, the culture was passed with a 1:5 to 1:10 dilution on days 1, 3, 5, and 7. By 7 days after electroporation, there was no longer any detectable plasmid DNA. Traces of CAT activity remained, however, as would be expected given the unusual stability of the CAT protein.

These results showed that the introduced DNA was gradually diluted out of the parasite population, with the slope indicating no significant replication of the introduced plasmid.

V. Stable Transformation of Obligate Intracellular Parasites

The development of several different methods to obtain stable transformation of obligate intracellular parasites is described below.

A. The Development of Drug-Based Selections for Stable Transformants

Experiments performed in support of the present invention have demonstrated that chloramphenicol, like the mechanistically similar antibiotic clindamycin (Pfefferkorn), has a potent parasiticidal effect on Toxoplasma, but the parasiticidal effects have delayed onset. Parasites complete 2–3 cycles of host cell lysis (approximately 7 days or 20–25 divisions) before any effect of chloramphenicol is evident.

Daily visual inspection of cultures indicated that 10 μM chloramphenicol killed over 90% of parasites, but had no obvious effects on the host monolayer. These results indicate that *Toxoplasma gondii* has a highly specific susceptibility to drugs inhibiting "prokaryotic" translation. This may reflect an unusual target for chemotherapy in these and other coccidian parasites such as the mitochondrion or other novel organelles.

Stable transfection via homologous recombination into the SAG1 gene seemed likely to be a deleterious event given that Toxoplasma tachyzoites are haploid and SAG1 is single-copy. Indeed, SAG1-mutants are somewhat disabled (Mineo, et al., 1993).

Figure 5:
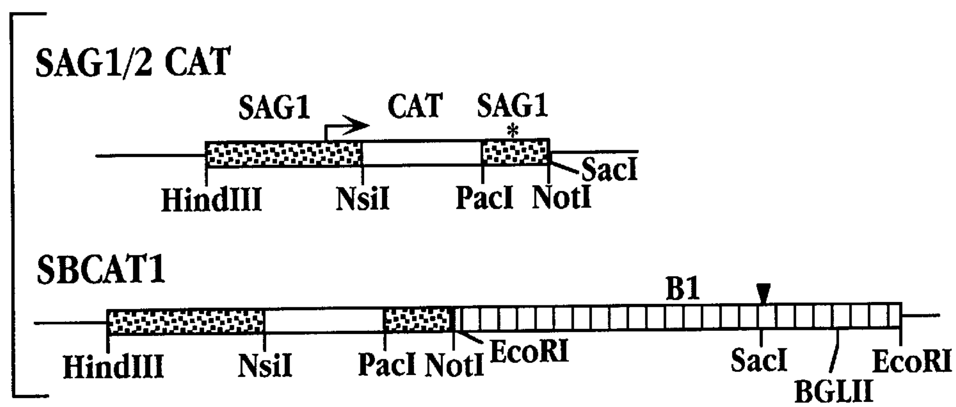
FIG. 5 shows schematic representations of expression vectors SAG1/2 CAT and SBCAT1.

A vector useful for stable parasite transformation was constructed (Example 6) by adding a segment of a gene B1 (Burg, 1989), which is tandemly duplicated approximately 35 times within the genome, to the SAG1/2 CAT expression vector construct described above. In transient transfection experiments, this B1-containing construct (SBCAT1) resulted in similar CAT activity as a construct without B1. An exemplary B1-containing expression vector, SBCAT1, is schematically shown in FIG. 5.

Circular or linearized plasmids were electroporated into freshly lysed tachyzoites using conditions described for transient transfection (Example 2). Parasites were then inoculated onto confluent monolayers of human foreskin fibroblasts (HFF) and allowed to infect and go through one lytic cycle in host cells before passage and initiation of selection (Example 7).

A preferred embodiment of the present invention provides for selection of transformed parasites with 20 μM chloramphenicol. Ten micromolar chloramphenicol provides an effective selection, but sometimes allowed growth of parasites which were not stably transformed with CAT sequences. Further, selection with 100 μM chloramphenicol did not yield any stable transformants. Accordingly, the chloramphenicol concentrations for use in the method of the present invention range from about 10 μM to less than 100 μM.

Figure 6:
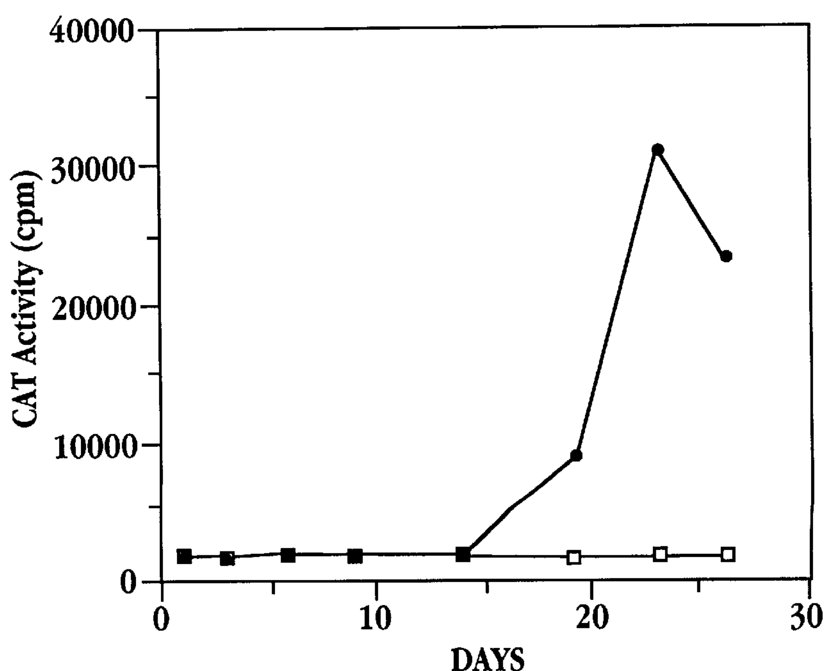
FIG. 6 presents representative CAT expression data for parasites transfected with SBCAT1 in the presence and absence of drug selection.

Using 20 μM chloramphenicol, emergence of chloramphenicol-resistant presumptive transformants was evident in transfected cultures after approximately 10 days of selection. High levels of CAT were detected in parasites transfected with both 10 and 40 μg of linearized SBCAT1 plasmid after approximately 2–3 weeks of selection (FIG. 6: 10 μg SBCAT1 transformants (diamonds), and control (squares)). No CAT activity was detectable in parasites transfected and passed in parallel without drug selection.

The minimum amount of plasmid required to yield stable recombinants varies depending upon the construct used. Experiments performed in support of the present invention indicate that titration of linearized plasmid between 1 and 50 μg usually yields stable transformants. Selection can be initiated as soon as 16 hours after transformation.

Parasites used in these experiments were cloned after 4–6 weeks of selection, but stably transformed parasites can be cloned as early as 10 days after transformation (when wild-type cells are dying and a chloramphenicol-resistant population is beginning to emerge).

When comparing CAT levels in transient assays, no difference was seen between equal amounts of linear or circular plasmid. However, circular plasmid seems to be less efficient as a source of stably transforming DNA. Exact quantitation of parasite survival in transfected populations was difficult due to the delayed effects of the drug and the necessity to pass parasites onto new monolayers during selection.

Figure 7:
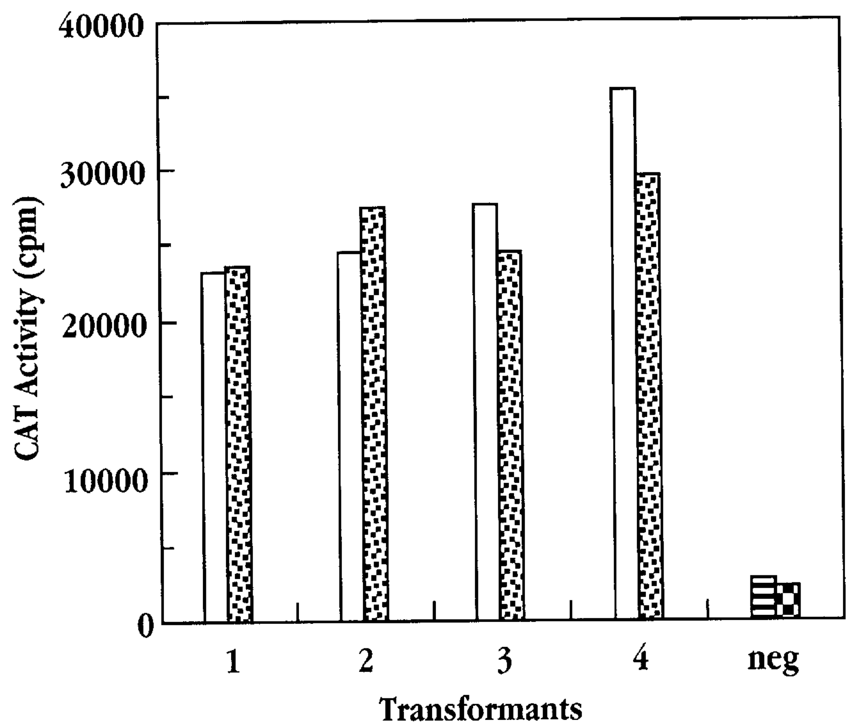
FIG. 7 shows data from CAT assays performed on transformed parasites grown in chloramphenicol (FIG. 7, hatched bars) or grown without drug (FIG. 7, solid bars) for two weeks. Data from non-transformed control parasites are also shown (neg).

Once selected, transformants did not require growth in drug for maintenance of CAT expression (Example 8, FIG. 7). Several clones have been maintained over 250 generations (12 weeks) in the absence of drug without any loss of CAT activity. Given this stability, it appeared unlikely that the gene was carried as an extrachromosomal element. To confirm this, preliminary genomic DNA hybridization analyses of clones from three separate experiments, transfected with 10 μg of the linearized SBCAT1 construct, were performed using a CAT gene-specific probe. Hybridization of uncut DNA did not indicate the presence of plasmid-sized extrachromosomal DNA. Instead the intensity and size of bands obtained with a variety of restriction enzymes suggested that multiple copies of the plasmid integrated into the genome.

Figure 8:
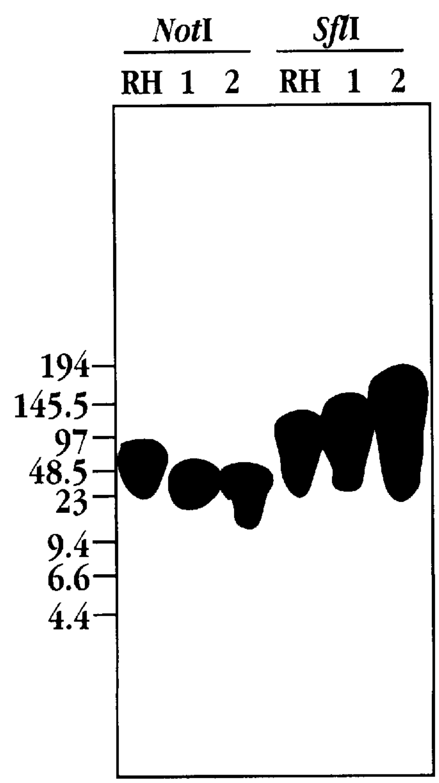
FIG. 8 presents genomic DNA hybridization data.

All clones continued to express p30, indicating that homologous recombination of the linearized plasmid had not occurred in SAG1. To test if integration had occurred in the B1 repeat locus, chromosomal plugs of representative clones from separate experiments were digested with Not I, an enzyme which cuts the plasmid vector but not the B1 repeat, and SfiI, which cuts in neither B1 nor the vector. Digests were then analyzed by pulsed field gel electrophoresis and Southern blotting (Example 9). Blots were hybridized with a B1 gene-specific probe (FIG. 8). The first recombinant parasite tested (FIG. 8, lane 2) had multiple copies of CAT integrated tandemly into the B1 tandem repeat as evidenced by the appearance of a plasmid-sized Not I fragment and two larger fragments (approximately 30 and 45 kb) and the disappearance of the original fragment (approximately 70 kb). Similarly SfiI digestion of DNA from clone 1 compared with the wild-type revealed a single larger SfiI fragment hybridizing to B1 probe (FIG. 8, lane 5).

A second recombinant had multiple copies of CAT which had integrated at separate sites within the B1 repeat locus as reflected by the presence of multiple B1-hybridizing fragments smaller than the B1 Not I fragment present in wild-type DNA (FIG. 8, lane 3). The SfiI fragment digest of this clone revealed a fragment which, as expected, was considerably larger than wild-type B1 SfiI fragment (FIG. 8, lane 6).

These data confirm the genomic integration of the expression vectors used to transform the parasites. Genomic DNA hybridization analysis of randomly isolated clones using a number of expression vectors further indicated that multiple copies of CAT had inserted randomly within the genome.

Genomic DNA hybridization analysis also demonstrated successful targeted insertion at the ROP1 locus. The plasmid ROP1/3 CAT (FIG. 9; Example 10), was constructed having 5' and 3' regions from ROP1 flanking the CAT sequences. Following transfection and selection for chloramphenicol-resistant clones, recombinants were screened by Western blot for the presence or absence of ROP1 protein. Two ROP1-deficient recombinants were identified.

Figure 11:
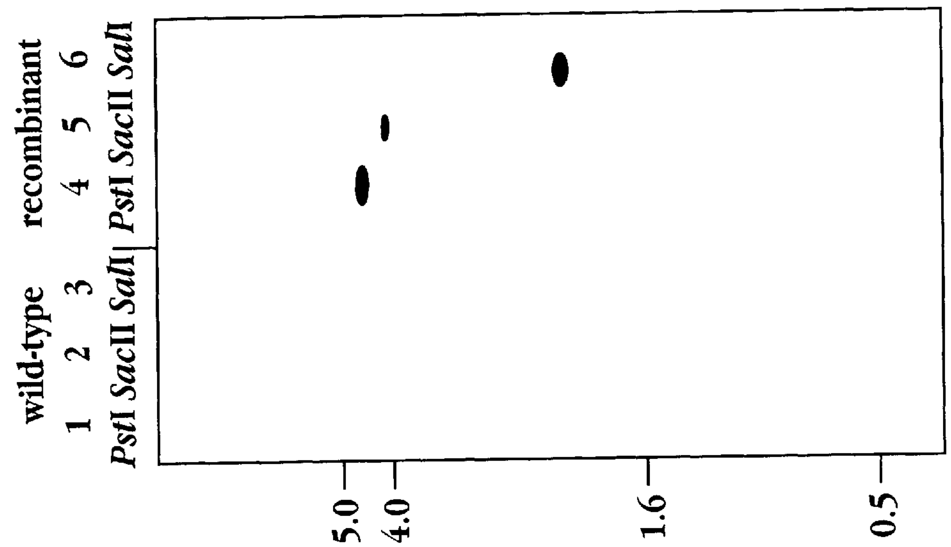
FIG. 11 presents genomic DNA hybridization data confirming that a single copy of ROP1/3 CAT had integrated into the ROP1 locus by homologous recombination.
Figure 10:
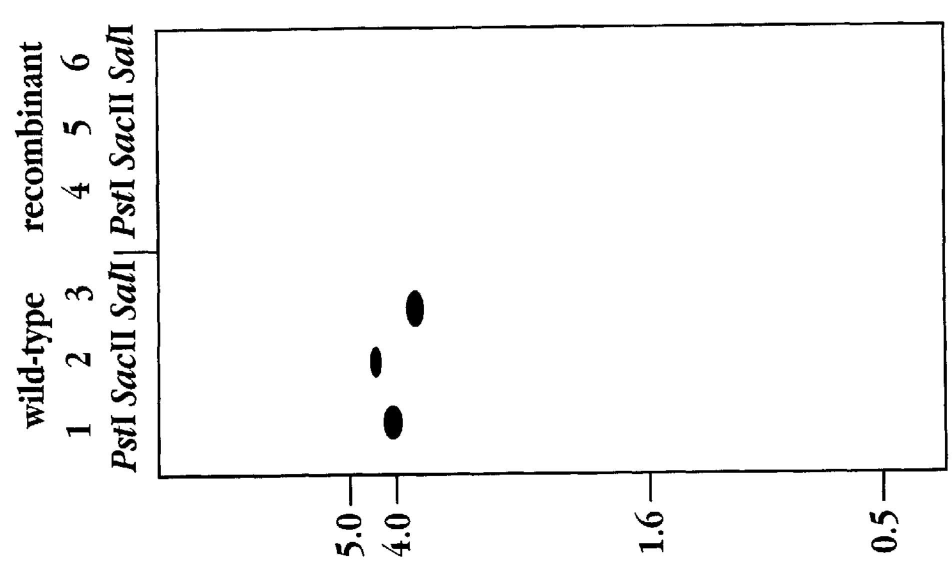
FIG. 10 presents genomic DNA hybridization data confirming that the coding region of ROP1 was no longer present.

DNA genomic hybridization analysis of one of the knock-out recombinants indicated that the coding region of ROP1 was no longer present (FIG. 10): a single copy of ROP1/3 CAT had integrated into the ROP1 locus by homologous recombination (FIG. 11).

This result supports the usefulness of the stable transformation method of the present invention for use in genetic manipulations (such as gene knock outs, gene replacements, etc.) of parasitic organisms.

Bleomycin and other members of the bleomycin family, such as phleomycin, can also be used to select stable transformants by the method of the present invention. When practicing this aspect of the present invention, a gene known to confer resistance to the drug is placed in the expression vector as a selectable marker gene: e.g., replacing the CAT coding sequences with the ble gene from Tn5 or *Streptoalloteichus hindustanus* (Jefferies, et al., 1993; Perez, et al., 1989; Gatignol, et al., 1987). The transfected parasites are typically pre-incubated with the drug before plating on the host cells. After plating, the host cells are cultured in the presence of the drug. A useful concentration range for the chosen drug can be readily determined by titration. Typically the concentration range is between about 2.5 μg/ml and 50 μg/ml. A phleomycin concentration of 5 μg/ml reduces background growth and allows selection of resistant transformants. The presence of the ble gene can be determined by standard DNA hybridization methods, as described above for CAT coding sequences.

B. The Development of Fluorescence Activated Cell Sorting Selection for Stable Transformants Experiments performed in support of the present invention demonstrate the ability to use surface antigens, expressed from a vector, combined with fluorescence activated cell sorting (FACS) to obtain stable transformants of obligate intracellular parasites. The following description of the use of the Toxoplasma SAG1 gene, in the practice of this aspect of the present invention, is exemplary of the general method. Other surface antigen genes may be useful in the practice of the invention, including (i) the gene encoding the p22 protein of Toxoplasma (Prince, et al., 1990), and (ii) genes encoding other Apocomplexa surface antigens (e.g., circumsporozoite protein of Plasmodium (Enea, et al., 1984).

The SAG1 gene of Toxoplasma encodes the major tachyzoite surface protein, p30. This protein has received attention as both a diagnostic reagent and as a potential component of a subunit vaccine. The SAG1 encoded protein is a major humoral and cellular antigen reactive with sera from Toxoplasma infected individuals. Recent studies have shown that purified SAG1 protects mice from lethal challenge (Buelow and Boothroyd, 1991). Further, studies have indicated that cellular invasion by Toxoplasma can be blocked by some monoclonal antibodies and polyclonal antisera specific for SAG1.

Toxoplasma mutants unable to express SAG1 encoded protein, or that express altered SAG1 encoded proteins, have been generated with ethylnitrosourea mutagenesis (Pfefferkorn, et al., 1976). One null mutant, sag1-, does not express SAG1 encoded protein due to a point mutation which creates stop codon midway through the coding sequence (Kasper, 1992b).

The sag1-( ) null mutant was transfected with the 1.6 kb AvaI genomic SAG1 fragment derived from the Toxoplasma strain RH (Example 11). Expression of the SAG1 encoded protein could be easily detected by Western blot in populations transfected 24 hours previously with SAG1 plasmid. Further, expression of the SAG1 encoded protein was evaluated by immunofluorescence using a monoclonal antibody specifically reactive with the SAG1 encoded protein (Example 11). Null mutants transfected with SAG1 coding sequences were inoculated onto HFF. At 24 hours and 48 hours, immunofluorescent microscopy revealed many vacuoles containing SAG1-positive parasites. These results indicate that the transfectants were viable and expressing the SAG1 coding sequences that had been introduced by transfection.

Analysis by flow cytometry employing the DG52 monoclonal antibody, specific for the SAG1 encoded protein (Example 11), determined that approximately 15–20% of parasites transfected with 100 μg of plasmid expressed the SAG1 encoded protein. The fraction of parasites expressing the SAG1 encoded protein was equivalent on 1 and 4 days after transfection. However, parasites had less detectable SAG1 encoded protein on their surface 4 days after transfection as judged by relative fluorescence. These results do not appear to be an artifact of transfection, since parasites transfected with an equal amount of SAG1/CAT plasmid consistently expressed high levels of CAT protein.

Expression of SAG1 was transient in most transfectants. The transfectants that fell in the top 17% of SAG1-encoded-protein expression were sorted (Example 11) and recultured at day 4 after transfection. Reanalysis of this population 11 days later indicated that less than 1% of parasites continued to express SAG1 encoded protein on their cell surface. From this group, the transfectants that fell in the top 0.5% of SAG1 encoded protein expression were sorted and returned to culture.

After 25 days of culture, 1–2% of parasites continued to express SAG1 encoded protein. Further sorting yielded a population which permanently expressed SAG1 encoded protein at wild-type levels. Clones isolated from this population (stable transfectants) were shown to express SAG1 encoded protein after culturing for a 5 month evaluation period (Example 12A).

Genomic DNA hybridization analysis of three stable transfectant clones, using SAG1-specific probe sequences, indicated that the three clones were siblings as all three gave identical patterns indicative of insertion into a random, nonhomologous site. One was therefore chosen for further analysis. DNA hybridization analysis (Example 12B, FIG. 15) indicated that a single copy of SAG1 had integrated into the genome. See FIG. 14 for restriction map of transforming SAG1 plasmid and genomic SAG1 locus. The stable transformant carried 2 copies of SAG1, the original genomic copy and the introduced copy, as reflected by the presence of an extra SAG1 band in each of the restriction digests.

The results disclosed above demonstrate that stable integration of transfected DNA is sufficiently efficient that stable parasitic recombinants can be identified and cloned using repeated rounds of FACS: linearized DNA may improve transformation efficiency.

FACS identification of stable parasite transformants should also be a useful technique for the cloning and investigation of other surface antigens. Monoclonal antibodies, immunoreactive with other surface antigens, may be obtained by standard methods (Harlow, et al., 1988). This method represents a relatively simple way to identify parasites which stably express various transfected genes, especially those which express surface antigens. Use of FACS enables the identification of stable transformants with no selective pressure, and thus identification of transformants likely results in identification of parasites with integrated DNA or carrying the plasmid in an extremely stable episomal form.

C. Maintenance of Exogenous DNA as a Stable Episome

Experiments performed in support of the present invention and described in Example 13 demonstrate that methods of the present invention may be used to produce obligate parasites stably-transformed with autonomously-replicating episomes. The episomes are composed of an *E. coli* plasmid into which random fragments of Toxoplasma DNA are inserted. The episomes are selected for those where the random DNA fragment(s) contain an "autonomously replicating sequence", or ARS, derived from the parasite genome.

Such sequences may be empirically identified, e.g., in the manner illustrated in Example 13. According to this approach, random fragments of DNA isolated or derived from the organism of interest or a related organism are cloned into a vector and introduced back into the Apicomplexan organism. The transformed organisms are grown for several passages to allow those plasmids that contain an ARS to be replicated and increase in relative proportion to those that have no such sequence. The parasites are then harvested and plasmid DNA is prepared and introduced into *E. coli* to allow for non-selective amplification. The amplified DNAs are then harvested as above and reintroduced into Toxoplasma. After several such rounds of selection and amplification, one can obtain sequences which are selectively able to be replicated in the Toxoplasma organisms without compromising the ability of the plasmids carrying them to replicate in *E. coli.*

Using such a protocol, combined with the transformation procedures described, a sequence which confers upon a plasmid the ability to be replicated and, with appropriate selection, maintained within Toxoplasma, was identified. This sequence, termed stability enhancing sequence 1 (SE1) is approximately 560 bp in length, and contains the sequence presented as SEQ ID NO:2 at its 5' end and the sequence presented as SEQ ID NO:1 at its 3' end. The entire sequence can be isolated by one of skill in the art using the teachings herein. For example, PCR primers can be designed based on SEQ ID NO:1 and SEQ ID NO:2, and the entire ~560 bp fragment can be isolated and sequenced using standard methods (see, e.g., Ausubel, et al.). Note that SE1 is a Sau3AI/KpnI fragment, facilitating its cloning into corresponding sites in a vector or plasmid. SE1, or sequences having the same function (e.g., sequences identified in a manner like that described in Example 13), may be incorporated into vectors of the present invention to stabilize such vectors as episomes in transfected obligate parasites of the present invention.

VI. Utility

The present invention includes a method of transforming obligate intracellular parasites of the phylum Apicomplexa. Parasites particularly amenable to transformation by the methods of the present invention include those belonging to the class Sporozoasida, subclass Coccidiasina. The subclass Coccidiasina includes the order Hemosporidia, which contains the genus Plasmodium, the causative agent of human malaria. Coccidiasina also includes the order Eucoccidiorida which includes the suborder Eimeriorina. Suborder Eimeriorina, includes, among others, the following genera: Toxoplasma, Eimeria, Sarcocystis, Neospora, Isospora, Cryptosporidium, Hammondia and Besnoitia.

A. Screening Anti-Parasite Compounds

The transformed parasites of the present invention are useful for screening compounds that generally block expression of a parasite's genes and specifically block expression from a particular promoter. For example, a reporter gene can be transformed into a selected host cell (such as, luciferase into HFF cells, where expression of the luciferase is mediated by human transcriptional and translational regulatory sequences). A second reporter gene (such as the CAT constructs described above) can be transformed into the parasite cell. The parasite can then be introduced into the host cell, the cells treated with a selected compound hoped to be therapeutically effective against the parasite. The levels of the two reporter gene products are then compared to identify compounds efficacious against the expression of parasite genes, but not against the host genes.

B. Vectors and Strain Variants

The present invention also provides vectors suitable for the transformation of obligate intracellular parasites. Such vectors can be sold individually or in kits for use in the transfection and transformation methods of the present invention. Kits may also include buffers useful for the transformation of the parasites or samples of parasites prepared for transformation. For example, parasite cells that have been treated with cytomix buffer and then frozen.

Further, such kits may also contain parasites that have been attenuated by transformation. For example, Toxoplasma is an incurable, potentially fatal pathogen in humans as well as animals, which can cause abortions in pregnant hosts. Other parasites can be dangerous to work with, as well.

The present invention furnishes the means to provide an attenuated parasite that is less dangerous, which can be used for routine studies. For example, in Toxoplasma a subset of genes is known to be expressed only in the tissue cyst or bradyzoite stage. Disruption of one or more of these genes may allow the generation of a strain which could not give rise to chronic infection. Thus, existing drug treatments for acute infection can destroy all the parasites and completely eliminate the infection.

The vectors and transformed parasite strains of the present invention are also useful for the expression of heterologous or exogenous genes that require eucaryotic post-translational processing (e.g., glycoproteins), since these obligate intracellular parasites carry out essentially all eucaryotic protein processing steps. Such strains may be a useful source of recombinant material for therapeutic purposes (such as, hormones and cytokines).

C. Vaccine and Antigen Production

Attenuated parasites can be constructed, using the methods of the present invention, and used as vaccines, not only for parasite antigens as well as against other infectious agents or cancer cells. For example, immunization of the female before pregnancy would be expected to protect the developing fetus and prevent abortion or other serious outcomes of Toxoplasma infection.

Attenuated parasites may be constructed by generating deletions of target parasite genes that disable the parasite in a selected capacity using the methods of the present invention. For example, such target genes may include those involved in the biosynthesis of key metabolites. Growth in vitro, in the presence of an excess of such a metabolite, would allow significant growth of the parasites. Upon infection into an animal, however, the growth would stop as the supply of the metabolite was exhausted and not replenished. By way of another example, a Toxoplasma with a knockout mutation of a sexual cycle gene can be generated. Such a manipulation will block Bradyzoite formation, thus avoiding the establishment of a chronic Toxoplasma infection. Bradyzoites are present in pseudocysts. The tachyzoite (product of the asexual reproductive cycle) infection can be cleared by treatment of antibiotics after the establishment of immunity. In addition, such a parasite can be used to express stage specific antigens under the control of a non-stage specific promoter: e.g., transformed Toxoplasma cells, in its tachyzoite stage, can express antigens specific to the latent/sexual phase. This parasite can be used as a vaccine to generate antibodies against the expressed sexual phase antigens, but the parasite is incapable of switching into the sexual stage, since it also carries a deletion in genes required for the switch.

Further, a single attenuated parasite pathogen could be used to express antigens from a number of related pathogens (e.g., members of the phylum Apicomplexa), so that the parasite can be used to generate immunity to a number of parasites. For example, antigens from Plasmodium can be expressed in attenuated Toxoplasma transformants. This transformant can then be used as a combined Toxoplasma/Plasmodium vaccine, or further, as a source of plasmodium antigen. Such an approach may also be used, for example, to produce a vaccine strain expressing, e.g., viral antigens. This approach has a large advantage over other vector systems in that the parasite processes and modifies its proteins in ways similar to other eukaryotes and different from bacteria. Further, unlike viruses (which can also carry and express foreign genes), these protozoa have the capacity to carry a large number of different genes.

Attenuated parasites may also be transformed with expression vectors carrying the coding sequences for proteins that stimulate immune response in the target host. For example, an attenuated Toxoplasma parasite may also express interleukin coding sequences that would make the vaccine strain stimulate the immune system as well as supply the antigen.

Attenuated parasites can also be used in an immunotherapy to boost antibody production against a selected epitope. The selected epitope can be cloned into an expression vector, a stably transformed attenuated parasite generated and the resulting parasite administered to an infected mammal to boost immune response to the selected epitope. For example, SAG1 recombinant antigen and a T-cell epitope can be expressed in the same parasite.

Veterinary, as well as human vaccines, can be developed. For example, chicken coccidiosis is one of the most serious diseases of the poultry industry. Engineering of the Eimeria parasites that cause coccidiosis might allow development of safe, non-reverting vaccine strains. Another example of veterinary vaccine is as follows. In Toxoplasma a subset of genes is known to be expressed in the sexual phase of Toxoplasma's life cycle, based on monoclonal antibody studies (Kasper, et al., 1984). Genes specifically associated with the sexual cycle can be knocked out, by the gene-replacement method described above, to generate a strain incapable of sexual reproduction. Such a strain would prevent transmission of the parasite from cats to humans.

Methods of the present invention can further be used to produce an Apicomplexa parasite stably-transformed with an expression vector encoding a reporter (e.g., the lacZ gene of *E. coli* encoding beta-galactosidase) that can be detected using, e.g., a calorimetric or fluorescence assay (Seeber and Boothroyd, 1996). Such reporter parasites may be employed, e.g., in high-throughput screens for identification of new anti-parasite drugs. They can also be used to infect animals being used for in vivo studies of anti-parasite drugs, since the presence and absence of the parasites in the animal's tissues (e.g., before and after treatment) can be readily detected using standard assays (e.g., calorimetric assays).

D. Diagnostics

The present invention also provides a source of recombinantly produced parasite antigens that can be used in diagnostic kits. For example, currently a large number of mice are sacrificed each year to make antigen for detection of Toxoplasma infection (typically in excess of 400,000 mice per year). Antigens are usually generated by interperitoneal injection of tachyzoites which results in ascites. Parasites derived from these ascites are used to detect reactive antibodies in humans or other mammals (such as, cats). Overexpression of a major antigen protein (e.g., SAG1) will generate similar quantity of antigen but using a reduced number of mice that have to be sacrificed.

The transfection/transformation method of the present invention also provides a means to improve the specificity of current diagnostics. For example, negative controls can be generated by making knockout deletions of diagnostic antigens. For Toxoplasma, such a control may use a deletion strain of SAG1. The deletion strain is grown and used to determine the background of an immunological test employing SAG1 encoded antigen.

The stable transformation method of the present invention also provides the ability to produce a variety of antigens in a single transformed parasite. Multiple antigens representing strain variations of a single pathogen (such as, Toxoplasma) can be expressed using a single transformed parasite. Further, strains can be engineered to produce antigen from a variety of different species of parasite (such as, Toxoplasma and Plasmodium). Strains producing multiple antigens can be used to generate test antigens for diagnostic uses. Expressing antigens from a number of parasitic sources by using a single parasite gets around the problem of having to grow all the different organisms.

E. Genetic Analysis

Recently, the potential of *T. gondii* as a genetic system has been realized through the analysis of phenotypic mutants (Kasper, et al. 1987) and the creation of a low-resolution genetic map used to localize mutant genes of interest (Sibley, et al., 1992a). The transfection method of the present invention complements this more classical genetic approach. The efficiency of the transient expression described herein makes possible detailed studies on the expression of genes important to the processes of invasion, drug resistance, and other aspects of the host-parasite interaction. Further, the transformed parasites of the present invention provide means for screening compounds (typically by employing the effects of such compounds on the expression of reporter genes) effective to interfere with these processes.

Stable transformation (employing selectable markers) of obligate intracellular parasites, in conjunction with analysis of mutants and utilization of transmission genetics, will allow the molecular dissection of the biology of intracellular parasitism.

The following examples illustrate, but in no way are intended to limit the present invention.

Materials and Methods

*E. coli* DNA polymerase I (Klenow fragment) was obtained from Boehringer Mannheim Biochemicals (Indianapolis, Ind.). T4 DNA ligase and T4 DNA polymerase were obtained from New England Biolabs (Beverly, Mass.); Transfer membranes were obtained from Schleicher and Schuell (Keene, N.H.).

Synthetic oligonucleotide linkers and primers were prepared using commercially available automated oligonucleotide synthesizers. Alternatively, custom designed synthetic oligonucleotides may be purchased, for example, from Synthetic Genetics (San Diego, Calif.). cDNA synthesis kit and random priming labeling kits were obtained from Boehringer-Mannheim Biochemical (BMB, Indianapolis, Ind.).

Standard molecular biology and cloning techniques were performed essentially as previously described in Ausubel, et al., 1988; Sambrook, et al., 1989 and Maniatis, et al. (1982).

Common manipulations involved in polyclonal and monoclonal antibodies were performed by standard procedures (Harlow, et al., 1988). Pierce or Promega (Madison, Wis.) are sources for many antibody reagents.

General protocols for flow cytometric analysis and clinical data analysis for flow cytometry are described in Keren, et al., (1989) and Coon, et al. (1991).

EXAMPLE 1

Construction of a Reporter Plasmid

Plasmid SAG1/2 CAT was constructed containing the chloramphenicol acetyltransferase (CAT) gene (Gorman, et al., 1982) and the upstream and downstream sequences of the *T. gondii* major surface antigen gene, p30 or SAG1 (Burg, et al., 1988).

SAG1/2 CAT was constructed by a two-step method. First, reverse polymerase chain reaction (PCR) (Triglia, et al., 1988) was performed with an "SK+BLUESCRIPT" vector (Strategene, La Jolla Calif.), containing the complete SAG1 gene, using primers that generate an Nsi I site at the second in-frame ATG and a Pac I site at the stop codon.

A CAT cassette with a Nsi I site embracing its ATG and a Pac I site encompassing its stop codon was generated by PCR and cloned into the corresponding Nsi I-Pac I sites of the SAG1 expression vector.

The "SK+BLUESCRIPT" vector provided sequences allowing the replication and selection of the vector constructs in a bacterial host. Other known bacterial vector systems (e.g., Clontech, Palo Alto Calif.) can be used in this capacity as well. Further, yeast vectors can be used in the practice of the present invention (e.g., Hitzeman, et al., 1988; Rutter, et al., 1988; Oeda, et al., 1988). The yeast transformation host is typically *Saccharomyces cerevisiae,* however, other yeast suitable for transformation can be used as well (e.g., *Schizosaccharomyces pombe*).

EXAMPLE 2

Transfection of Parasite Cells

A. Transfection of *Toxoplasma gondii*

*Toxoplasma gondii* tachyzoites (RH strain) were grown in Human Foreskin Fibroblasts (HFF) cells until the infected cultures had spontaneously lysed. They were then purified by passage through Whatman CF-11 cellulose (Tanabe, et al., 1977) and harvested by centrifugation at 1000 g for 15 min.

The resulting material was washed twice by resuspension in electroporation buffer [120 mM KCl, 0.15 mM $CaCl_2$, 10 mM $K_2HPO_4$-$KH_2PO_4$ (pH 7.6), 25 mM Hepes (pH 7.6), 2 mM EDTA (pH 7.6), and 5 mM $MgCl_2$] (Van den Hoff, et al., 1992) and harvested as just described.

Either $5\times10^6$ HFF or $1\times10^7$ *T. gondii* tachyzoites were resuspended in 0.8 ml of cytomix buffer supplemented, just before use, with 2 mM adenosine triphosphate (pH 7.6) and 5 mM glutathione. Further, one of the following is mixed with each sample: either 0.1 ml of cytomix buffer alone or 0.1 ml of cytomix buffer containing 25 pmol of SAG1/2 CAT circular plasmid isolated from a cesium chloride gradient.

Each mixture was then transferred to an electroporation cuvette (4-mm gap) (BTX, San Diego, Calif.) and exposed to an electric pulse with an electroporator (BTX Electro Cell Manipulator 600) in the high-voltage mode ("2.5 kV/RESISTANCE"): the charging voltage set to 2.0 kV, the resistance set at 48 ohm ("R3"). The resulting discharge voltage was approximately 1.4 kV with a pulse length of 0.40 to 0.45 ms.

Electroporated cells were incubated at room temperature for 15 min. The cells were transferred into an enriched culture medium (DMEM) (Burg, et al., 1988) with 20% "NU SERUM" (Collaborative Research Inc., Bedford, Mass.) containing 0.04% gentamicin and incubated for 16 hours at 37° C. This material was harvested and washed at 4° C. in 0.25 M Tris-HCl (pH 7.8). After resuspension in 100 $\mu$l of 0.25 M tris-HCl (pH 7.8), the cells were frozen and thawed three times. The lysate was cleared by centrifugation in an Eppendorf Microfuge (10,000 g) for 10 min.

Transformed parasites can be inoculated into monolayers of HFF cells.

EXAMPLE 3

Chloramphenicol Acetyltransferase Expression In Transfected Cells

Radioactively labeled chloramphenicol was incubated in lysates of cells transfected with the CAT expression construct SAG1/2 CAT. CAT activity was assayed in a mixture of 0.25 M tris-HCl (pH 7.8), 1 mM acetyl coenzyme A, 0.3 $\mu$Ci of [$^{14}$C]chloramphenicol (50 to 60 mCi/mmol; Amersham) in a final volume of 100 $\mu$l. The reaction mix was incubated at 37° C. for 16 hours, extracted with ethylacetate, and dried. The pellet was resuspended in 27 $\mu$l of ethylacetate and spotted on a thin-layer chromatography plate (PE SIL G, Whatman).

After development for 2 hours with chloroformmethanol (95:5), the plates were dried and analyzed with a "PHOSPHOR IMAGER" (Molecular Dynamics). The results are presented in FIG. 1: lane 1, HFF not transfected; lane 2, HFF transfected with the plasmid; lane 3, HFF mixed with *T. gondii* parasites and the plasmid but without electroporation; lane 4, *T. gondii* parasites mixed with plasmid but without electroporation; and lane 5, *T. gondii* parasites transfected with the plasmid. In the figure, migration of unacetylated chloramphenicol (Cm), the two monacetylated forms (M), and the diacetylated form (D) relative to the origin (0) are indicated.

These results show that CAT activity is present only in *T. gondii* parasites transfected with the SAG1/2 CAT plasmid, demonstrating the ability to transfect the parasite.

EXAMPLE 4

Alternative Expression Plasmids

CAT gene expression was evaluated in $10^7$ extracellular *T. gondii* parasites transfected by electroporation with 50 pmol of three different *T. gondii* expression vectors (FIG. 2).

Conditions for electroporation and CAT assay are described above. The CAT assay were analyzed by thin-layer chromatography and the results are presented in FIG. 3: SAG1/1 CAT (lane 1), SAG1/2 CAT (lane 2), ROP1/1 CAT (lane 3), ROP1/2 CAT (lane 4), TUB1 CAT (lane 5), TUB1/inv. CAT (lane 6), and SK CAT (lane 7). In the figure, migration of unacetylated chloramphenicol (Cm), the two monacetylated forms (M), and the diacetylated form (D) relative to the origin (O) are indicated.

These results demonstrate the ability of several parasite genes to direct the express of a reporter gene in a parasitic host. Specifically, SAG1 gene sequences (SAG 1/2 CAT expression vector), ROP1 gene sequences (ROP 1/2 CAT expression vector) and TUB1 gene sequences (TUB1 CAT expression vector).

EXAMPLE 5

Transience of Transfection in the Absence of Selection

The transience of transfection was analyzed on two populations of recombinant parasites electroporated with 25 pmol of either TUB1 CAT or ROP1/2 CAT plasmids. Parasites ($5\times10^7$) were electroporated with 25 pmol of either TUB1 CAT or ROP1/2 CAT plasmids and inoculated into monolayers of HFF. One day later, lysis of the host cell was complete, and the recombinant parasites were harvested and counted. One-fifth to one-tenth (usually $\sim1\times10^7$ parasites) of the population was inoculated and expanded in HFF until they lysed again 2 days later.

In parallel, cell lysates were prepared from $5\times10^7$ parasites and assayed for CAT activity, and total DNA was extracted from $5\times10^7$ parasites and subjected to Southern (DNA) blot analysis. The same procedure was repeated until day 9 after electroporation.

FIGS. 4A and 4B show the results of equal numbers of successive generations of parasites transfected with TUB1 CAT and ROP1/2 CAT at days 1, 3, 5, 7, and 9 after electroporation when assayed for CAT activity (in the linear range) with the solvent phase-partition method as described (Neuman, et al., 1987).

Total DNA was extracted from $10^7$ parasites and transferred by slot blotter, in duplicate, to nylon membranes. The presence of CAT DNA sequences was detected by Southern blot analysis with a 600-bp DNA fragment encoding the CAT sequence. Signals for each point were normalized to the same amount of total DNA with signals obtained by hybridization of the duplicate with a single-copy Toxoplasma gene probe. The probes were labeled by the random primer method with $^{32}$p-labeled deoxycytidine 5'-triphosphate, and the spots were quantified by "PHOSPHOR IMAGER."

The results of these hybridization analyses are presented in FIGS. 4C and 4D.

Comparison of the data presented in FIGS. 4A/4B and 4C/4D show the relationship between decreasing DNA concentration and decreasing CAT activity. Traces of CAT activity remain after all detectable CAT DNA has disappeared. This result is likely due to the unusual stability of the CAT protein and/or rare parasite lines in which the transfecting plasmid has become stably retained.

EXAMPLE 6

Construction of the SBCAT1 Expression Vector The starting plasmid SAG1/2 CAT has been described above and is graphically represented in FIG. 5. Briefly, SAG1/2 CAT 1 is composed of "BLUESCRIPT II SK+" (Stratagene, La Jolla, Calif.; FIG. 5, thin line), containing SAG1 upstream and downstream regions (FIG. 5, hatched boxes) fused to CAT (FIG. 5, grey box). The plasmid contains approximately 800 bp upstream of the AUG start codon of the SAG1 gene and 300 bp downstream of the stop codon.

The transcription start site (FIG. 5, bent arrow) and polyadenylation site (FIG. 5, "*") are indicated. An EcoRI genomic DNA fragment containing a single B1 repeat (FIG. 5, wavy box) was ligated to SacI-cut, phosphatased SAG1/2 CAT after treatment of both with T4 DNA Polymerase, destroying the SacI cloning site. The resulting plasmid, SBCAT1, was linearized at the remaining SacI site within the B1 repeat (FIG. 5, arrow) for use in transformation.

EXAMPLE 7

Stable Transformation of Parasites $1\times10^7$ *T. gondii* tachyzoites were resuspended in 0.8 ml of cytomix buffer supplemented, just before use, with 2 mM adenosine triphosphate (pH 7.6) and 5 mM glutathione. Further, one of the following is mixed with each sample: either 0.1 ml of cytomix buffer alone or 0.1 ml of cytomix buffer containing 25 pmol of SBCAT1 plasmid isolated from a cesium chloride gradient.

Each mixture was then transferred to an electroporation cuvette (4-mm gap) (BTX, San Diego, Calif.) and exposed to an electric pulse with an electroporator (BTX Electro Cell Manipulator 600) in the high-voltage mode ("2.5 kV/RESISTANCE"): the charging voltage set to 2.0 kV, the resistance set at 48 ohm ("R3"). The resulting discharge voltage was approximately 1.4 kV with a pulse length of 0.40 to 0.45 ms.

Electroporated cells were incubated at room temperature for 15 min. Each sample was divided and inoculated onto two T25 flasks of confluent HFF growing in Dulbecco's Modified Eagle's Medium (DMEM; Gibco/BRL, Gaithersburg, Md.) (Burg, et al., 1988) with 10% "NU SERUM" (Collaborative Research Inc., Bedford, Mass.), 2 mM glutamine and 20 μg/ml gentamicin. One flask was harvested for CAT activity 1 day after transfection by scraping the infected monolayer and syringing through a 27 gauge needle.

The remaining culture was lysed after 3 days and was inoculated onto new monolayers with and without 20 μM chloramphenicol (water-soluble chloramphenicol; Sigma, St. Louis, Mo.). Five to ten percent of the culture ($2\text{–}5\times10^6$ parasites) was passed as host cells lysed. Cultures treated with drug that did not lyse host monolayers within 5–7 days, due to dying chloramphenicol-sensitive parasites, were scraped, syringed and passaged using 20–25% of the lysate.

At a concentration of 20 μM chloramphenicol, chloramphenicol-resistant transformants were evident in transfected cultures after approximately 10 days of selection. The level of CAT activity (determined as described above) was high in parasites transfected with both 10 and 40 μg of linearized SBCAT1 plasmid after approximately 2–3 weeks of selection. Representative data for parasites transfected with 10 μg of SBCAT1 is presented in FIG. 6.

CAT assays were performed using the solvent phase-partition assay (Neuman, et al., 1987) on $10^7$ parasites transfected with 10 μg linearized SBCAT1 and maintained in the presence (FIG. 6, solid squares) or absence (FIG. 6, open squares) of 20 μM chloramphenicol. Chloramphenicol selection was begun three days after transfection. Data is presented with all assays in the linear range of detection. Days after transfection are indicated in the figure.

The initial transient expression of CAT seen in the first 1–6 days after transfection is not detectable by the phase-partition CAT assay using 10 μg DNA and this number of parasites. It can only be detected using the more sensitive thin-layer chromatographic method.

In the absence of drug selection, no CAT activity was detectable in parasites transfected and passed in parallel. Stable transformants transfected with 10 μg plasmid were cloned and subjected to further analysis.

EXAMPLE 8

Stability of CAT Expression in Transformed Parasites

Parasites transformed with 10 μg SBCAT1 were cloned by limiting dilution in the presence of 10 μM chloramphenicol after six weeks of selection. Only wells containing a single plaque were used. CAT assays were performed on transformed parasites grown in chloramphenicol (FIG. 7, hatched bars) or grown without drug (FIG. 7, solid bars) for two weeks. Each number signifies a separate individual clone of a transformed parasite. Negative controls (neg) include parasites transfected with a plasmid lacking CAT (clear bar) and an assay performed with no lysate (wavy bar). CAT assays were performed using $10^7$ parasites.

The results of these experiments indicate that, after initial transformation and selection, sustained selection is not required for the maintenance of stably transformed parasites.

EXAMPLE 9

Genomic DNA Hybridization Analysis of Transformed Parasites

Chromosomal plugs of parasite genomic DNA were prepared as previously described (Sibley, 1992b) from wild-type RH strain and cloned stable transformants, obtained after transformation with SBCAT1. Plugs were digested in situ with 100 U of NotI or SfiI (New England Biolabs) overnight as suggested by the manufacturer.

Pulsed field gel electrophoresis was performed using a “GENELINE I TAFE” (Beckman) apparatus using a two-step program consisting of 150 V, 30 second switch for 10 hours followed by 150 V, 15 second switch for 10 hours. The plugs were electrophoresed in 1% LE agarose (FMC, Philadelphia, Pa.) in 0.25% TAE (Maniatis, et al., 1982).

The resulting gel was stained with ethidium bromide and UV crosslinked with 60 mJoules before transfer to nylon membranes by alkaline capillary transfer (Maniatis, et al., 1982; Ausubel, et al., 1988). The membrane was probed with the 2.2 kb B1 gene fragment (Burg, 1989) which was labelled by random priming with $^{32}$p dCTP. The membrane was washed at 65° C. with 0.1×SSC/0.25% “SARKOSYL” for 1 hour and exposed at −70° C. A lambda DNA ladder and lambda phage DNA cut with HindIII were used as size standards. A resulting autoradiogram is presented in FIG. 8.

In the figure, RH indicates wild-type parasites, 1 a representative clone from experiment 1, and 2 a representative clone from experiment 2.

EXAMPLE 10

Knockout of the Genomic ROP1 Gene

Figure 9:
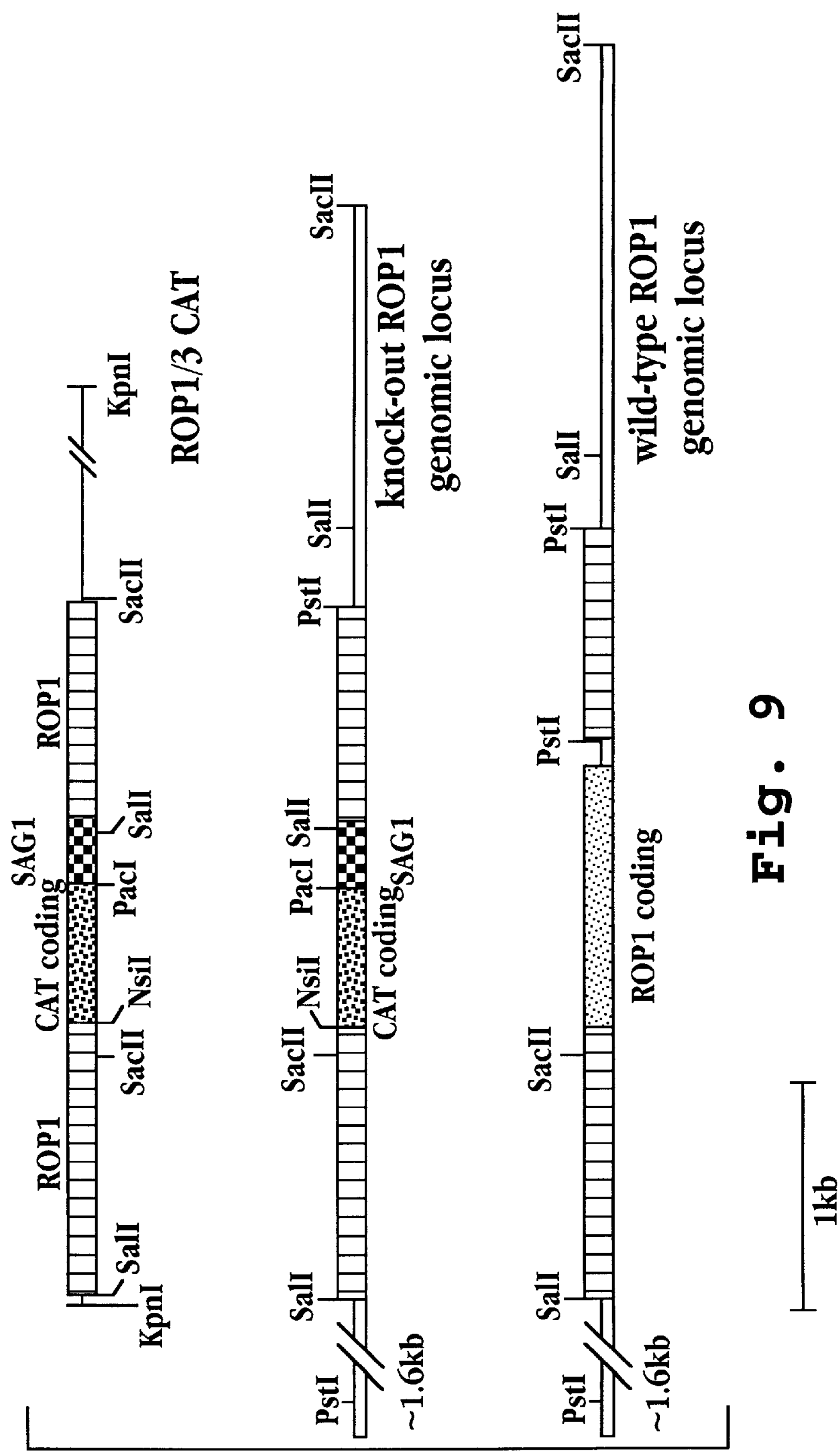
FIG. 9 presents a schematic diagram of the ROP1/3 CAT construct.

FIG. 9 presents a schematic diagram of the ROP1/3 CAT construct used in the following transformations. ROP1/3 CAT was cloned by insertion of a 950 bp PstI fragment from the downstream region of ROP1 into BamHI-cut phosphatased ROP1/2 CAT. Insert and plasmid were treated with T4 DNA Polymerase and all four dNTPs prior to ligation, thus destroying the BamHI cloning site on the vector and the PstI sites on the insert.

The ROP1/3 CAT contains approximately 1.3 kb of ROP1 upstream sequence including the promoter and 5' untranslated region (from genomic SalI site to 2nd AUG), 600 bp of CAT coding region (embraced by NsiI and PacI sites which contain the start and stop codons respectively), 300 bp of SAG1 3' region (identical to that in constructs in FIG. 5 and containing polyadenylation and presumptive termination signals), and the 950 bp PstI fragment from the ROP1 3' untranslated and downstream region.

In FIG. 9: the thin line indicates “BLUESCRIPT II SK+” vector sequences; vertical lines indicate ROP1 regions in the construct; clear boxes indicate ROP1 genomic sequences not present in the plasmid. ROP1 coding region, CAT coding region and SAG1 sequences are indicated. ROP1/3 CAT was linearized for transfection at the KpnI site in the polylinker.

Toxoplasma transfection was performed using 20 μg ROP1/3 CAT plasmid linearized with KpnI. Selection with 20 μM chloramphenicol was begun 16 hours after transfection. Parasites were cloned by limiting dilution, in the presence of drug, 10 days after transfection.

Genomic DNA from wild-type RH parasites (FIGS. 10 and 11, lanes 1–3) and the ROP1 knock-out recombinant (FIGS. 10 and 11, lanes 4–6) were digested with PstI (FIGS. 10 and 11, lanes 1 and 4), SacII (FIGS. 10 and 11, lanes 2 and 5), and SalI (FIGS. 10 and 11, lanes 3 and 6) in duplicate. The resulting DNA fragments from these digests were size fractionated by gel electrophoresis and the DNA fragments transferred to membranes. The membranes were probed in parallel with a 1.2 kb fragment encompassing the exact ROP1 coding region (FIG. 10) or a 600 bp CAT fragment (FIG. 11) (both labelled by random priming with $^{32}$P dCTP). The membranes were washed at a final stringency of 0.2×SSC/0.1% SDS at 65° C.

Homologous replacement is most clearly seen in the PstI digest where the wild-type 4.2 kb fragment (lane 1, FIG. 10) has been replaced with a 4.7 kb fragment in the recombinant (lane 4, FIG. 11) reflecting the loss of the 2nd genomic PstI site and the difference in size between the CAT plus SAG1 sequences and the ROP1 coding sequence they replace.

EXAMPLE 11

Generation of Stable Transformants Using Selection by Fluorescence Activated Cell Sorting A. Tissue Culture Conditions Toxoplasma PLK strain is a clonal derivative of a primary sheep isolate designated ME49 (Kasper, et al., 1985). A SAG1 nonsense mutant derived from this Toxoplasma line (Kasper, et al., 1987) was obtained from L. Kasper, Dartmouth Medical School. Parasites were grown in confluent monolayers of human foreskin fibroblasts (HFF) maintained in DMEM (Gibco BRL/Life Technologies, Gaithersburg Md.) supplemented with 10% Nuserum (Collaborative Research) 2 mM glutamine and 50 ug/ml gentamicin.

Parasites were harvested by scraping infected monolayers and syringing through a 27 gauge needle. Parasites were purified from host cell debris by passage over 3.0 micron polycarbonate filters (Nucleopore Corporation).

B. Transfection

Figure 14:
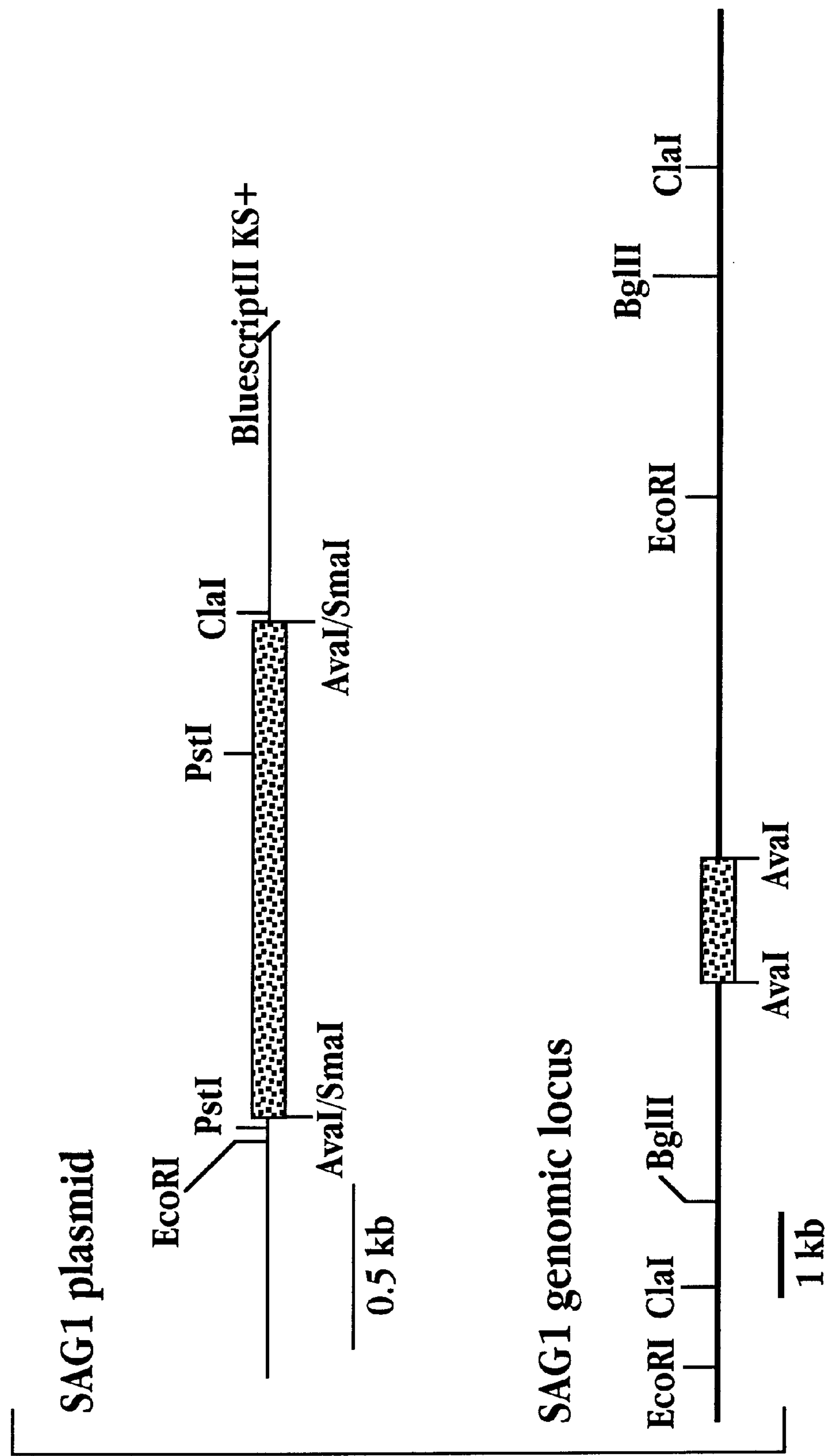
FIG. 14 presents a restriction map of the SAG1 transforming plasmid and the SAG1 genomic locus.

A 1.6 kb genomic SAG1 clone (Burg, et al., 1988) and expression plasmid SAG1/2 CAT, described above, were isolated from CsCl gradients by standard methods (Maniatis, et al., 1982). FIG. 14 presents a restriction map of the SAG1 transforming plasmid and the SAG1 genomic locus. Approximately 100 $\mu$g plasmid DNA was mixed with $2\times10^7$ sag1- parasites in cytomix (120 mM KCL, 0.15 mM $CaCl_2$, 10 mM $K_2HPO_4/KH_2PO_4$ pH 7.6, 25 mM Hepes pH 7.6, 2 mM EGTA pH 7.6, 5 mM $MgCl_2$, 2 mM ATP, 5 mM glutathione) and electroporated essentially as described above using a BTX electroporator set to 2.0 kV/48 ohms in the high resistance mode. Transfected cells were incubated at room temperature for 15 minutes and then inoculated directly onto monolayers.

C. Immunofluorescence

HFF were plated onto microscope slides and grown to confluence. Transfected parasites were resuspended in complete media and inoculated onto subconfluent monolayers. Untransfected wild-type parasites and sag1- parasites were inoculated onto the slides in parallel.

After 48 hours the slides were washed in PBS and fixed for 20 minutes in 2.5% formaldehyde/PBS. Slides were incubated for 10 minutes in PBS/0.05% Saponin and blocked using DMEM/1% FCS/0.01"SAPONIN." All subsequent steps included Saponin at 0.01%.

Host cells and parasite nuclei were labeled using Hoechst dye (Harlow, et al., 1988).

Slides were incubated at room temperature with the SAG1-specific mouse monoclonal antibody DG52 (Burg, et al., 1988) diluted 1:1000 in DMEM/1% FCS/Saponin for 1 hour. The slides were washed three times, ten minutes for each wash, using PBS/Saponin. The slides were incubated with fluorescein labelled goat anti-mouse immunoglobulin diluted 1:1000 and Hoechst diluted to in DMEM/1% FCS/Saponin. Slides were washed in PBS/Saponin and observed on an Olympus microscope.

Immunofluorescence of transfectants inoculated onto HFF after transfection at 24 hours and 48 hours revealed many vacuoles containing SAG1-positive parasites indicating transfectants were viable. Further, the transfectants appeared to divide normally.

Both the null mutant and wild-type parasite were stained in parallel and used as control comparisons.

D. Fluorescence Activated Cell Sorting (FACS)

All incubations and washes were done at room temperature in complete media supplemented with 10 mM Hepes pH 7.0. Purified parasites were incubated for 30 minutes at room temperature with mouse monoclonal antibody DG52 diluted 1:1000. Parasites were washed 3 times and then incubated for 30 minutes with fluorescein-conjugated goat antisera specific for mouse immunoglobulin (Cappel, Durham, N.C.; Pierce, Rockford, Ill.) diluted 1:1000 (other fluorescent labels (Pierce), in addition to fluorescein, can be used to generate flourescently labeled antibodies). After washing 3 times, parasites were analyzed with a "FACSTAR" Fluorescence Activated Cell Sorter (Becton-Dickinson).

Positive cells were sorted into complete media and inoculated onto HFF or cloned into 96 well plates of confluent HFF. One week after cloning, plates were visually inspected and wells containing single plaques were further characterized.

Expression of SAG1 was transient in most transfectants as determined by flow cytometry analysis using the DG52 monoclonal antibody. Transfectants that fell in the top 17% of SAG1-encoded-protein expression were isolated by fluorescence activated cell sorting (FACS) and recultured at day 4 after transfection.

The resulting population of transfected parasites was evaluated for the expression of the SAG1 encoded protein after 11 days of culture. Flow cytometry analysis indicated that less than 1% of parasites continued to express SAG1 encoded protein on their cell surface. Using FACS, the transfectants that fell in the top 0.5% of SAG1 encoded protein expression were sorted and returned to culture.

After 25 days, 1–2% of parasites continued to express SAG1 encoded protein. The FACS was repeated on this population. The transfectants that fell in the top 0.5% of SAG1 encoded protein expression were sorted and returned to culture. Three rounds of sorting yielded a population permanently expressing the SAG1 encoded protein at wild-type levels.

FIG. 12 presents a schematic of FACS selection and sorting of stable transfectants.

EXAMPLE 12

Characterization of Transformants Selected by FACS

A. Western Blot Analysis

Cloned transformants were maintained in continuous culture for 5 months after transfection (over 300 generations). Proteins from approximately $10^6$ parasites were separated on a 12% PAGE gel under non-reducing conditions and transferred to a nitrocellulose membrane (Schleicher and Schuell, Keene, N.H.).

The membrane was blocked with PBS/1% nonfat milk/0.05% "TWEEN 20" and probed with monoclonal antibody DG52 diluted 1:1000 in PBS/1% nonfat milk/0.05% "TWEEN" 20. After washing 3 times in PBS/0.05% "TWEEN" 20, the membrane was incubated with horseradish peroxidase coupled to goat anti-mouse immunoglobulin antisera (diluted 1:1000).

The membrane was washed, treated with Enzymatic ChemiLuminescense (ECL) detection agents (Amersham), according to the manufacturers instructions. The membrane was then exposed to Kodak "XRP" film. The resulting autoradiogram is presented in FIG. 13. In the figure, the lanes are as follows: (1) wild-type PLK parasites, (2) cloned transformant 2, (3) cloned transformant 1, and (4) sag1-4 mutant parasites. Sizes of molecular weight markers in kilodaltons is indicated.

The results of this analysis indicate the absence of SAG1 encoded protein in he sag1-4 mutant, and the presence of the protein in the wild-type and transformed strains.

B. DNA Isolation and Southern Analysis

Parasites were purified from freshly lysed cultures, washed with PBS, and lysed with DNA lysis buffer (120 mM NaCl, 25 mM TrisHCl pH 7.5, 10 mM EDTA, 1% Sarkosyl) supplemented with 0.100 mg/ml RNAse A. After incubation for 30 minutes at 37° C., 1 mg/ml of Proteinase K was added and the suspension was incubated at 55° C. overnight. The solution was extracted twice with phenol and twice with chloroform/isoamyl alcohol (24:1) before precipitation with 2 volumes of ethanol. The resulting DNA pellet was washed with 70% ethanol and resuspended in TE (10 mM TrisHCl pH 8.0, 1 mM EDTA).

Approximately 3–4 μg of DNA was cut with a 10–20 fold excess of enzyme according to the manufacturers instructions. DNA from the null mutant sag1-4 (M) and transformant (T) was separated on a 0.6% agarose gel in TAE buffer. Samples included uncut mutant DNA, uncut mutant DNA supplemented with 200 pg SAG1 plasmid, uncut transformant DNA. Further, the samples included M and T DNA cut with BglII, ClaI and EcoRI. Size of molecular weight markers are indicated in kilobases.

DNA was transferred to nylon membranes by alkaline capillary transfer. Membranes were probed with a 1.2 kb SAG1 PstI fragment (obtained from SAG1 plasmid; Burg, et al., 1988) labeled with $^{32}$P-dCTP by random priming.

The membranes were washed for 1 hour at a final stringency of 0.1×SSC/0.25% Sarkosyl at 65° C. before exposure to Kodak "XAR" film at −70 degrees.

Genomic DNA hybridization analysis (Maniatis, et al., 1982; Ausubel, et al., 1988) indicated that a single copy of SAG1 had integrated into the genome of each transfectant (FIG. 15). FIG. 14 shows a restriction map of the SAG1 transforming plasmid and of the genomic SAG1 locus.

Comparison of the hybridization patterns of uncut transformant DNA with mutant DNA supplemented with SAG1 plasmid DNA indicated that the extra copy of SAG1 was not carried as a plasmid-sized extrachromosomal element. Digestion with BglII, an enzyme which does not cut within the plasmid, revealed a new larger fragment in addition to the endogenous BglII fragment. This result indicates that the plasmid integrated into the Toxoplasma genome at a site outside the SAG1 locus.

EXAMPLE 13

Construction of a Vector Capable of Autonomous Replication in Toxoplasma

A genomic DNA library was generated by partially-digesting Toxoplasma DNA with Sau3AI and cloning the resulting fragments (approx size range 4–6 kb) into the BamHI site of a modified pUC19 plasmid. The pUC19 plasmid was modified by adding, into the AflIII site, a 90 bp cassette possessing a NotI site flanked by two AscI sites, each about 40 bp away from the NotI site. Fifty μg of this library was introduced into $1\times10^7$ Toxoplasma by electroporation as described above in Example 2. The transfected parasites were then allowed to infect a T25 HFF host cell monolayer as described above.

Following several days of growth, parasites were recovered as described in Example 11 and DNA was isolated using a modified protocol of Medina-Acosta and Cross (1993). The isolated DNA was used to transfect *E. coli* host cells (DH12) using standard electroporation methods, and the cells were then grown on plates containing 100 μg/ml ampicillin to transformed cells. The selected cells were expanded and the plasmid DNA prepared and introduced back into Toxoplasma as described above.

Following four cycles of this selection in the two hosts, individual colonies of *E. coli* were grown, each containing one of the plasmids that survived the selection. Five of these plasmids were expanded and then individually introduced into Toxoplasma parasite populations. The pUC19-derived parent vector was used as a negative control ("vector only" control).

The results indicate that all five recombinants showed a marked increase in stability compared with the vector only control. One of the five was randomly chosen for further analysis. Restriction enzyme mapping indicated that this plasmid had an insert of about 6,500 base pairs. To identify a smaller portion of this insert which could also confer autonomous replication, the ~6.5 kb insert was digested with restriction enzymes into overlapping fragments of 1–4 kb, each of which was cloned into the original vector and electroporated into the parasite as described above. Following about four lytic cycles for the parasite, DNA was recovered and the number of plasmids analyzed by introducing the DNA into *E. coli* and selecting for ampicillin resistance. The results showed only that one PstI fragment (~1.9 kb) was able to confer stability on the vector. Additional analyses showed that the stability-enhancing elements were contained in a ~560 bp fragment having the sequence represented as SEQ ID NO:2 at its 5' end, and the sequence represented as SEQ ID NO:1 at its 3' end.

These results demonstrate that a fragment of DNA isolated according to the guidance presented herein may be incorporated into an expression vector used to transform Apicomplexa parasites as described above in order to stabilize maintenance of the vector as an episomal element.

While the invention has been described with reference to specific methods and embodiments, it will be appreciated that various modifications and changes may be made without departing from the invention.

It is claimed:

1. A transformed obligate intracellular parasite of the order Eucoccidiorida, containing a DNA sequence exogenous to said intracellular parasite.

2. A host cell containing the transformed parasite of claim 1.

3. A transformed parasite of claim 2, wherein said parasite is of the suborder Eimeriorina.

4. A transformed parasite of claim 3, wherein said parasite is of a genus selected from the group consisting of Eimeria, Sarcocystis, Neospora, Cryptosporidium, Hammondia and Besnoitia.

5. A transformed parasite of claim 1, where said DNA sequence encodes a gene useful for genetic selection.

6. A transformed parasite of claim 1, where said DNA sequence is integrated at a genomic DNA site of said transformed parasite.

7. A transformed parasite of claim 6, where said DNA sequence disrupts a gene present at said genomic site.

8. A transformed parasite of claim 1, where said DNA sequence is extra-chromosomal.

9. A transformed parasite of claim 1, where said DNA sequence is flanked by regulatory sequences derived from said parasite, and where said regulatory sequences are effective to allow expression in said parasite of said DNA sequence.

10. A transformed parasite of claim 9, wherein said regulatory sequences are derived from the group of genes consisting of SAG1, ROP1 and TUB1.

11. A transformed parasite of claim 5, where said gene encodes chloramphenicol acetyltransferase.

12. A method for the recombinant expression of a protein in a host infected with an obligate intracellular parasite of the order Eucoccidiorida, comprising introducing into said parasite a vector containing an exogenous DNA sequence encoding a protein, where said exogenous DNA sequence is flanked by regulatory elements effective to allow expression of the encoded protein in a parasite host cell, infecting said host with the parasite, and culturing the host under conditions permissive for the expression the protein.

13. The method of claim 12, where said vector includes a second DNA sequence which encodes a gene useful for genetic selection in parasite cells, where said DNA sequence is flanked by regulatory elements effective to allow expression of the sequence in the parasite cell.

14. A method for transfecting an obligate intracellular parasite of the order Eucoccidiorida, comprising, introducing into said parasite a vector containing a DNA sequence, and identifying a transfected parasite by selecting for the presence of said vector in said parasite.

15. The method of claim 14, where said DNA sequence encodes a surface antigen and said identifying further includes selecting parasites that express said antigen.

16. The method of claim 15, where said parasite is of the suborder Eimeriorina.

17. The method of claim 16, where said parasite is of a genus selected from the group consisting of Eimeria, Sarcocystis, Neospora, Cryptosporidium, Hammondia and Besnoitia.

18. The method of claim 15, where the parasite, before transformation, is unable to express a surface antigen normally expressed by the parasite, and where said DNA sequence contains a functional copy of a gene encoding said surface antigen.

19. The method of claim 14, where said DNA sequence encodes a gene useful for genetic selection in parasite cells, where said DNA sequence is flanked by regulatory elements effective to allow expression of the sequence in the parasite cells.

20. The method of claim 14, where said DNA sequence encodes chloramphenicol acetyltransferase.

21. The method of claim 14, where said transfecting includes the integration of the vector at a genomic site.

22. The method of claim 21, where said vector further includes a second DNA sequence which is homologous to a portion of said genomic site.

23. The method of claim 14, wherein said introducing is accomplished by electroporation.

24. The method of claim 14, where said identifying further includes plating the transfected parasites onto a layer of host cells.

25. The method of claim 24, where said transfecting includes the integration of the vector at a genomic site, and where said vector further includes a second DNA sequence which is homologous to a portion of said genomic site.

26. The method of claim 25, where said genomic site is the B1 locus.

27. The method of claim 15, where said selecting is accomplished by (i) exposing transformed parasite cells to fluorescently labeled antibodies, which are immunoreactive with said surface antigen, and (ii) isolating cells to which said antibodies have attached.

28. The method of claim 27, where said isolating is accomplished by fluorescence activated cell sorting.

* * * * *

SEQUENCE LISTING

```
(1) GENERAL INFORMATION:

   (iii) NUMBER OF SEQUENCES: 2


(2) INFORMATION FOR SEQ ID NO:1:

     (i) SEQUENCE CHARACTERISTICS:
          (A) LENGTH: 200 base pairs
          (B) TYPE: nucleic acid
          (C) STRANDEDNESS: double
          (D) TOPOLOGY: unknown

    (ii) MOLECULE TYPE: DNA (genomic)

   (iii) HYPOTHETICAL: NO

    (iv) ANTI-SENSE: NO

    (vi) ORIGINAL SOURCE:
          (C) INDIVIDUAL ISOLATE: 3' end sequence of SE1 fragment

    (xi) SEQUENCE DESCRIPTION: SEQ ID NO:1:

TTAACTGCAC CAAAGACTGC GTACTTTGAG CGTCCATGGT GTTCGATAAC GGAAAAAACA     60

CTTGCGAGTG TACGGCGAGT TGTGGTGCTG AATGAACAGA AAACTCCTTT GAACGCTGAC    120

ACGAGACAGC ACAGTTTGGG AGACAGCGAT CGGGGTGCTG CCTGGGAGTG TCACCGCATG    180

CATGCACGAT CCCCGGTACC                                                200


(2) INFORMATION FOR SEQ ID NO:2:

     (i) SEQUENCE CHARACTERISTICS:
          (A) LENGTH: 311 base pairs
          (B) TYPE: nucleic acid
          (C) STRANDEDNESS: double
          (D) TOPOLOGY: unknown

    (ii) MOLECULE TYPE: DNA (genomic)

   (iii) HYPOTHETICAL: NO

    (iv) ANTI-SENSE: NO

    (vi) ORIGINAL SOURCE:
          (C) INDIVIDUAL ISOLATE: 5' end sequence of SE1 fragment

    (xi) SEQUENCE DESCRIPTION: SEQ ID NO:2:

GGATCACTTC CGCGATGTCC GATGAAACGT GATGGCTATC CCGAATTCCT TTTTTTAAGG     60

ATATGGCTGC AGCCTTTGAC ATCTGTTTTT CTTTCTGTCT ATCCATGATT AAACGAAACG    120

TGTTAAGCGT TGTCAGCAAT GTGCAACCAG GGATCTGAGG ATTTCTGCAG ACAATCGGAT    180

TTCCAAGACA TTTTTTGGCA AGCGCGTTTT CACCCACACA CTAGATACTT CGTGTCATGC    240

GGTGTATTTC GTGTATTTAC AAAACCTACG ACCTCCCACT AAACGTTTCG GGTTCTTTCC    300

CGCGTTGACG G                                                         311
```